US006716421B2

(12) United States Patent
Brode, III et al.

(10) Patent No.: US 6,716,421 B2
(45) Date of Patent: Apr. 6, 2004

(54) DEVICES AND METHODS FOR ELIMINATING TERMITE COLONIES

(75) Inventors: Philip Frederick Brode, III, Cincinnati, OH (US); Garry Steven Garrett, Fairfield, OH (US); Leo Timothy Laughlin, Mason, OH (US); Randall Stryker Matthews, Cincinnati, OH (US); Dale Edwin Barker, Hamilton, OH (US); Daniel James Kinne, Cincinnati, OH (US); Gary Eugene McKibben, Middletown, OH (US); Christopher Miles Miller, Milford, OH (US); Timothy Robert Probst, Cincinnati, OH (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 09/799,184

(22) Filed: Mar. 5, 2001

(65) Prior Publication Data

US 2002/0172658 A1 Nov. 21, 2002

(51) Int. Cl.[7] .......................... A01N 31/00; A01N 33/02; A01N 37/00; A01N 37/02; A01N 37/06; A01N 43/40; A01N 43/54; A01N 43/66; A01N 25/00; A01N 25/02; A01N 25/08

(52) U.S. Cl. ................. 424/84; 424/DIG. 11; 424/646; 43/131; 43/132.1; 43/124; 514/23; 514/24; 514/25; 514/27; 514/32; 514/33; 514/34; 514/35; 514/42; 514/43; 514/53; 514/54; 514/183; 514/222.2; 514/228.8; 514/243; 514/244; 514/245; 514/247; 514/277; 514/315; 514/317; 514/327; 514/329; 514/331; 514/332; 514/335; 514/352; 514/354; 514/355; 514/356; 514/361; 514/364; 514/381; 514/394; 514/395; 514/399; 514/400; 514/407; 514/417; 514/460; 514/471; 514/532; 514/533; 514/544; 514/546; 514/616; 514/617; 514/619; 514/620; 514/622; 514/633; 514/637; 514/646; 514/648; 514/657; 514/734; 514/729; 514/730; 514/731; 514/736

(58) Field of Search .................. 424/84, DIG. 11, 424/646; 514/23–25, 27, 32–35, 42–43, 53–54, 317, 332, 335, 546, 646, 729, 730, 183, 222.2, 228.8, 243, 244, 245, 247, 255, 277, 315, 327, 329, 331, 352, 354–356, 361, 364, 381, 394, 395, 399, 400, 407, 417, 460, 471, 532, 533, 544, 616, 617, 619, 620, 622, 633, 637, 648, 657, 731, 734, 736; 43/131, 132.1, 124

(56) References Cited

U.S. PATENT DOCUMENTS

| 4,363,798 A | 12/1982 | D'Orazio |
| 4,468,405 A | 8/1984 | Rigterink et al. |
| 4,504,468 A | 3/1985 | Brill et al. |
| 4,873,084 A | * 10/1989 | Sallay ........................ 424/658 |
| 5,023,327 A | 6/1991 | Yamaoka et al. |
| 5,024,832 A | 6/1991 | Omata et al. |
| 5,039,693 A | * 8/1991 | Okada et al. ................ 514/406 |
| 5,096,710 A | 3/1992 | Minagawa et al. |
| 5,300,293 A | 4/1994 | Minagawa et al. |
| 5,609,879 A | 3/1997 | Myles |
| 5,637,298 A | 6/1997 | Stowell |
| 5,695,776 A | 12/1997 | Ballard et al. |
| 5,756,114 A | 5/1998 | Peterson |
| 5,778,596 A | 7/1998 | Henderson et al. |
| 5,811,461 A | 9/1998 | Hackler et al. |
| 5,874,097 A | 2/1999 | Henderson et al. |
| 5,885,606 A | 3/1999 | Kawada |
| 5,886,221 A | 3/1999 | Sbragia et al. |
| 5,899,018 A | 5/1999 | Gordon et al. |
| 5,901,496 A | 5/1999 | Woodruff |
| 5,921,018 A | 7/1999 | Hirose et al. |
| 5,925,368 A | 7/1999 | Voris et al. |
| 5,927,001 A | 7/1999 | Ballard et al. |
| 5,950,356 A | 9/1999 | Nimocks |
| 5,961,383 A | 10/1999 | Janssen et al. |
| 5,973,162 A | 10/1999 | Alig et al. |
| 6,003,266 A | 12/1999 | Woodruff |
| 6,016,625 A | 1/2000 | Bishoff et al. |
| 6,023,879 A | 2/2000 | Katz et al. |
| 6,025,397 A | 2/2000 | Soragia et al. |
| 6,037,344 A | 3/2000 | Wren |
| 6,058,646 A | 5/2000 | Bishoff et al. |
| 6,070,357 A | 6/2000 | Hartill et al. |
| 6,079,150 A | 6/2000 | Setikas et al. |
| 6,172,051 B1 | 1/2001 | Renello |

FOREIGN PATENT DOCUMENTS

| AU | 678129 B | 5/1997 |
| AU | 702813 B2 | 10/1997 |

(List continued on next page.)

OTHER PUBLICATIONS

EUROPATFULL on STNONLINE, accession No. 503320, claims of EP 503320 in English (1992).*

(List continued on next page.)

*Primary Examiner*—John Pak
(74) *Attorney, Agent, or Firm*—Brian S. Steinberger; Law Offices of Brian S. Steinberger, P.A.

(57) ABSTRACT

This invention relates to devices, kits, and methods for eliminating termite colonies. The kits, devices, and methods employ a termiticidal bait matrix containing a) a termiticide selected such that the termiticide causes death to about 50 to about 100% of termites within about 24 to about 84 days after the termites begin to ingest the termiticide or the bait matrix comprising the termiticide, b) a cellulose containing material, and c) water.

The termiticidal bait matrix can be used in a bait station installed in the ground. The kits are suitable to be used by consumers in their homes.

15 Claims, 9 Drawing Sheets

FOREIGN PATENT DOCUMENTS

| | | |
|---|---|---|
| CN | 1233392 A | 11/1999 |
| DE | 19831987 | 1/2000 |
| EP | 0125155 A1 | 4/1983 |
| EP | 503320 * | 9/1992 |
| EP | 0 503 320 B1 | 12/1995 |
| EP | 0587117 B1 | 1/1998 |
| EP | 0836917 A1 | 4/1998 |
| EP | 0846417 A1 | 6/1998 |
| EP | 0923864 A1 | 6/1999 |
| EP | 0968652 A1 | 1/2000 |
| FR | 2655240 | 6/1989 |
| FR | 2707455 A1 | 1/1995 |
| GB | 2231797 | 11/1990 |
| GB | 2231798 | 11/1990 |
| GB | 2243297 | 10/1991 |
| GB | 2290472 | 1/1996 |
| GB | 2315217 A | 1/1998 |
| JP | S52-41223 | 3/1977 |
| JP | 52041223 A | 3/1977 |
| JP | S56-140905 | 11/1981 |
| JP | 5 9205 391 A | 11/1984 |
| JP | 6 2029 504 A | 7/1985 |
| JP | 0931683 B | 12/1989 |
| JP | 02111702 | 4/1990 |
| JP | 05236985 | 9/1993 |
| JP | 06016609 A | 1/1994 |
| JP | H6-87707 | 3/1994 |
| JP | H8-5761 B | 1/1995 |
| JP | 10324608 A | 12/1998 |
| JP | H11-193206 A | 7/1999 |
| JP | 11163578 | 1/2000 |
| JP | 10255731 | 3/2000 |
| WO | WO 9323998 A1 | 12/1993 |
| WO | WO 9427434 A1 | 12/1994 |
| WO | WO 9600783 A1 | 1/1996 |
| WO | WO 9632009 A1 | 10/1996 |
| WO | WO 9819995 | 5/1998 |
| WO | WO 9833377 A1 | 8/1998 |
| WO | WO 9834481 | 8/1998 |
| WO | WO 0019816 A1 | 4/2000 |
| WO | WO 0027187 A2 | 5/2000 |
| WO | WO 0036914 A1 | 6/2000 |
| WO | WO 00/62610 A1 | 10/2000 |

OTHER PUBLICATIONS

Behr, et al., "Influence of Wood Hardness on Feeding by the Eastern Subterranean Termite, Reticulitermes flavipes (Isoptera: Rhinotermitidae)," Annals of the Entomological Society of America, vol. 65, No. 2, 1972, pp. 457–460.

Shultz, et al., "Palladium—A New Inhibitor of Cellulase Activities," *Biochem. Biophys. Res. Comm.*, vol. 209, No. 3, 1995, pp. 1046–1052.

* cited by examiner

DEVICES AND METHODS FOR ELIMINATING TERMITE COLONIES

FIELD OF THE INVENTION

This invention relates to devices and methods for eliminating termite colonies. More particularly, this invention relates to bait matrices and bait stations for eliminating termite colonies and methods for their use.

BACKGROUND

Termites have a social hierarchy with several general adult forms: workers, soldiers, secondary reproductives, and a primary male (king) and primary female (egg-laying queen). Workers make up the largest part of the colony, and among their tasks is foraging for food for the members of the colony. Workers are the colony members that cause damage to wood. Workers communicate information related to sources of food from one termite to another by chemical odor (pheromones) communication and touch (tactile) communication. Workers also carry food from its source back to the colony where it is shared with other colony members by trophallaxis.

Quick kill of individual foraging workers does not affect the main colony because it has no effect upon those hatching in the nest. Only the feeding termites are affected, those in the nest continue to multiply and thus the infestation remains. However, if a "slow acting" termiticide is mixed with a food source desirable to termites, the foraging workers will communicate the location of the food source to other workers, and the foraging workers will also carry the termiticide containing food back to the nest to be shared. If sufficient termiticide is transported back into the nest, it is possible to eliminate the entire colony.

One problem in eliminating a termite colony is locating the colony. Various species of termites may have nests that are subterranean, within the structure of homes, or "aerial" (in trees, under roofs, etc.). Subterranean termites include *Reticulitermes flavipes* (Eastern subterranean termites), *Reticulitermes hesperus*, *Reticulitermes virginicus*, *Coptotermes formosans* (Formosan termites), and *Heterotermes aureus*. Other types of termites include dry wood termites such as *Kaloterines minor*, *Kaloterines snyderi*, *Kalotermes schwarzi*, and *Procryptotermes hubbardi*; damp-wood termites such as *Prorhinotermes simplex*; rotten-wood termites such as *Zootermopsis angusticollis* and *Zootermopsis nevadensis*; powder-post termites such as *Cryptotermes brevis*; and nasutiform termites such as *Nasutitermes corniger*.

Attempts have been made to address the problems discussed above by the use of bait stations containing bait matrices. Some of the products currently available include FIRSTLINE® from FMC Corporation of Philadelphia, Pa., SUBTERFUGE™ from American Cyanimid of Madison, N.J., and SENTRICON® made by DowAgroSciences of Indianapolis, Ind. SENTRICON®, for example, is a termite colony elimination system consisting of a bait station in the form of a plastic spike container and a nontermiticidal bait matrix that is replaced with a termiticidal bait matrix containing a chemical insecticide when termites are detected at the nontermiticidal bait matrix. The system is designed for insertion in and around buildings and structures. SENTRICON® is only available at considerable expense from a licensed pest control operator ("PCO"). Typically, the PCO will install a plurality of bait stations containing the nontermiticidal bait matrix in the soil around the foundation of the structure to be monitored and protected. The PCO contracts to visit the site periodically after installation to check the bait stations for evidence of termite infestation or feeding on the bait matrix. If termite presence is detected in a bait station, the nontermiticidal bait matrix is replaced with a termiticidal bait matrix (containing a chemical insecticide). The PCO continues to visit the site periodically and replace spent termiticidal bait matrix until the colony is eliminated.

The chemical insecticide in SENTRICON® is hexaflumuron, a benzoylurea compound. Benzoylurea compounds (such as hexaflumuron, flufenoxuron, lufenuron, and dimilin) are chitin synthesis inhibitors, which disrupt the molting cycle of termites. However, chitin synthesis inhibitors suffer from the drawback that they are too slow-acting. It can take 4 months to 1 year to eliminate a termite colony using hexaflumuron in this way.

SUMMARY OF THE INVENTION

This invention relates to devices and methods for detecting the presence of termites and eliminating termite colonies. The devices and methods typically employ cellulase inhibitors as termiticides. Cellulose (in the form of wood, paper, etc.) is a source of food for termites. Termites require cellulases to digest the cellulose to glucose. Without wishing to be bound by theory, it is thought that cellulase inhibitors ingested by a termite prevent one or more of the cellulases in the gut of the termite from digesting cellulose, at least to some degree, e.g., a degree sufficient to kill the termite.

DETAILED DESCRIPTION OF THE INVENTION

Figure 1:
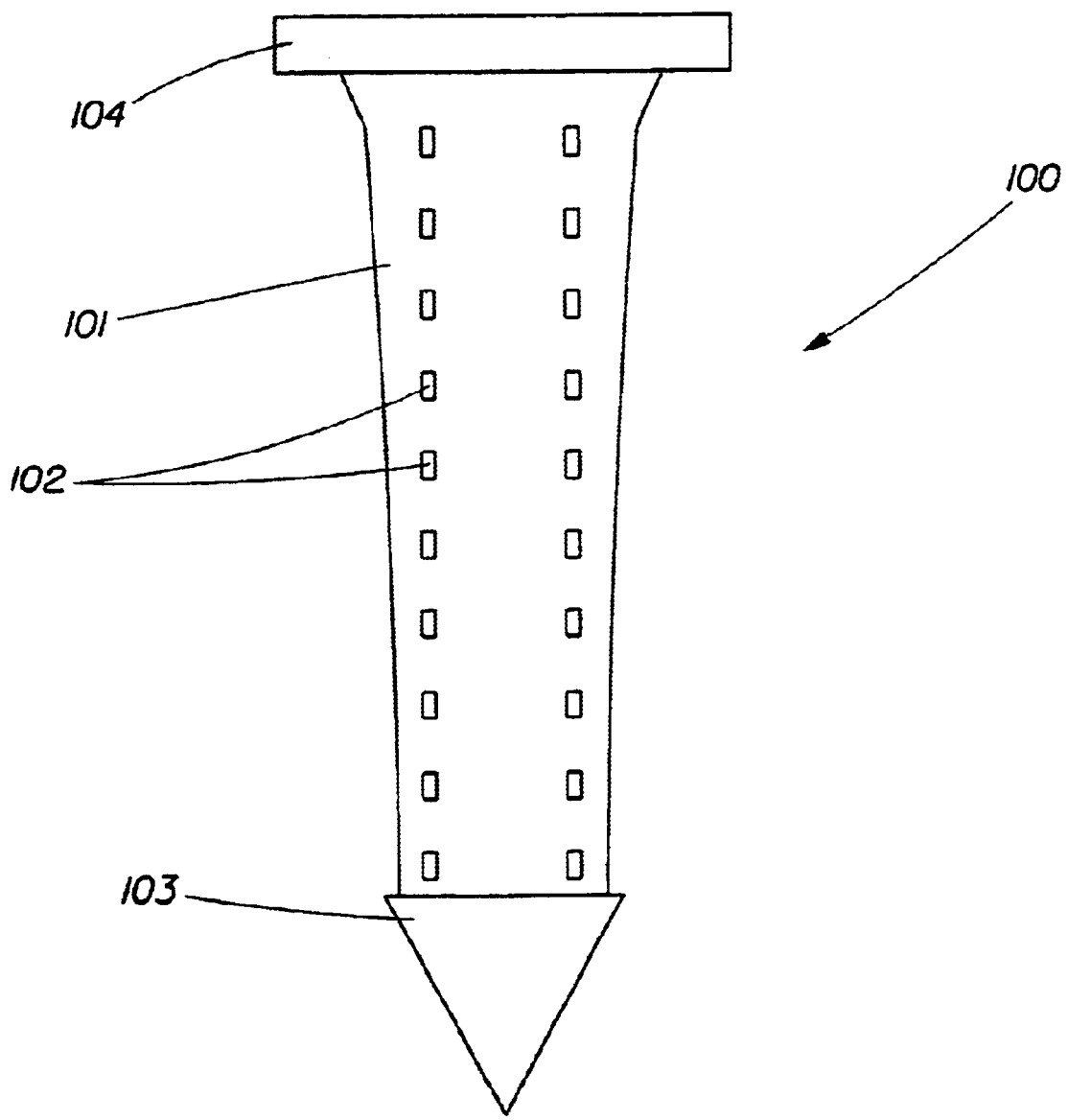
FIG. 1 is a bait station according to this invention.

Publications and patents are referred to throughout this disclosure. All U.S. Patents cited herein are hereby incorporated by reference.

All percentages, ratios, and proportions used herein are by weight unless otherwise specified.

Definitions

The following is a list of definitions for terms, as used herein.

"Attractant" means a compound that stimulates foraging termites to locate and/or feed on compositions containing the compound over other compositions and/or their regular food source.

"Cellulase" means a member of a class of enzymes that digest cellulose into glucose. Cellulase is a general term for any of the enzymes that together make-up the cellulase complex.

"Cellulase complex" means a natural enzyme mix of multiple exoglucanases, endoglucanases, and β-glucosidase as well as other enzymes produced by most organisms that produce cellulases.

"Cellulase inhibitor" means a compound, alone or in combination, that prevents one or more of the cellulases in the gut of a termite from digesting cellulose, at least to some degree, e.g., a degree sufficient to kill the termite. Preferred cellulase inhibitors are specific to cellulase, i.e., they do not inhibit or change the action of many proteins other than cellulases. More preferred cellulase inhibitors do not inhibit or change the action of proteins found in animals other than termites, particularly humans. Most preferred cellulase inhibitors, for purposes of this invention, do not inhibit or change the action of any proteins other than cellulases.

"Feeding stimulant" means a compound that increases the amount that termites eat of compositions containing the compound over other compositions and/or their regular food source.

"Heteroatom" means an atom other than carbon e.g., in the ring of a cyclic group or the chain of a substituted hydrocarbon group. Preferably, heteroatoms are selected from the group consisting of sulfur, phosphorous, nitrogen and oxygen atoms. Groups containing more than one heteroatom may contain different heteroatoms.

"Hydrocarbon group" means a chain of carbon atoms, preferably about 1 to about 6 carbon atoms, more preferably about 1 to about 3 carbon atoms. Hydrocarbon groups may have a linear or branched chain structure. Preferred hydrocarbon groups are saturated. Unsaturated hydrocarbon groups have one or more double bonds, one or more triple bonds, or combinations thereof. Hydrocarbon groups may be substituted or unsubstituted.

"Substituted" means one or more hydrogen atoms bonded to carbon atoms in the chain of a hydrocarbon group or the ring of a cyclic group have been replaced with other substituents and/or one or more carbon atoms in the chain of a hydrocarbon group or the ring of a cyclic group have been replaced with one or more heteroatoms.

"Trophallaxis" means transfer of gut content or food from a termite to other colony members.

Bait Matrix

This invention relates to bait matrices. The bait matrices can be termiticidal or nontermiticidal. The termiticidal bait matrices can be used to eliminate a termite colony. The nontermiticidal bait matrices can be used to monitor for the presence of termites.

The termiticidal bait matrix comprises: a) a termiticide, b) a cellulose containing material, and c) water. The termiticidal bait matrix may further comprise d) one or more optional ingredients.

Ingredient a) is a termiticide. The termiticide is typically selected such that it causes death to about 50 to about 100% of termites within about 24 to about 84 days after the termites begin to ingest the termiticide or a bait matrix comprising the termiticide. Preferably, the termiticide causes death to about 50 to about 100% of termites within about 38 to about 70 days after the termites begin to ingest the termiticide or a bait matrix comprising the termiticide.

Suitable termiticides in this invention include compounds of Formula I, below:

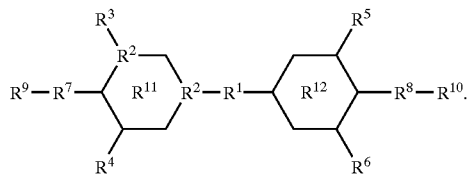

In formula I, $R^1$ is selected from the group consisting of a bond, a hydrocarbon group, O, and $NR^{14}R^{15}$. $R^1$ is preferably a hydrocarbon group having 1 to 6 carbon atoms, more preferably 1 to 3 carbon atoms. $R^1$ is preferably an unsubstituted hydrocarbon group. $R^{14}$ and $R^{15}$ are each independently selected from the group consisting of a hydrogen atom and a hydrocarbon group.

Each $R^2$ is independently selected from the group consisting of CH, a carbon atom, and a heteroatom. Preferably, the heteroatom is nitrogen. More preferably, $R^2$ is CH.

$R^3$, $R^4$, $R^5$, and $R^6$ are each independently selected from the group consisting of hydrogen atoms and hydroxyl groups. When $R^8$ and $R^7$ are oxygen atoms and $R^9$ and $R^{10}$ are hydrogen atoms, then $R^3$, $R^4$, $R^5$, and $R^6$ may alternatively be hydrocarbon groups of 1 to 6 carbon atoms.

$R^7$ and $R^8$ are each independently selected from the group consisting of hydrogen, oxygen, and nitrogen atoms. Preferably, $R^7$ and $R^8$ are each independently selected from the group consisting of oxygen and nitrogen atoms.

$R^9$ and $R^{10}$ are each independently selected from the group consisting of nil (i.e., when $R^7$ and/or $R^8$ are hydrogen atoms), hydrocarbon groups of 1 to 6 carbon atoms, alkyl esters of 1 to 6 carbon atoms, and amides. Preferably, $R^7$ and $R^8$ are oxygen atoms and $R^9$ and $R^{10}$ are hydrogen atoms.

$R^{11}$ and $R^{12}$ are each independently selected from the group consisting of saturated, unsaturated, and aromatic groups.

Examples of compounds of Formula I are shown below in Table I.

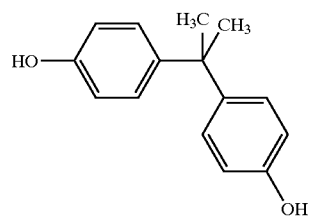

CAS No. 80-05-7

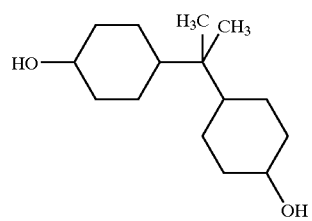

CAS No. 80-04-6

-continued

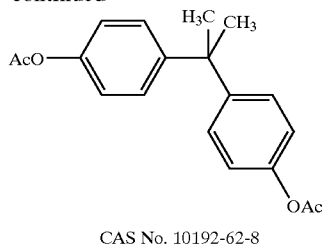
CAS No. 10192-62-8

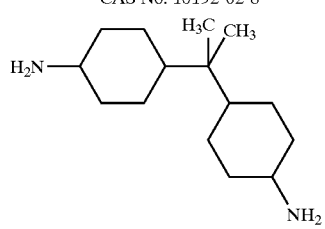

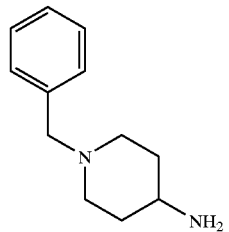
CAS No. 50541-93-0

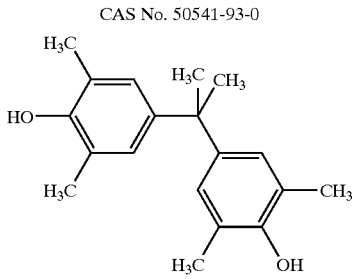
CAS No. 5613-46-7

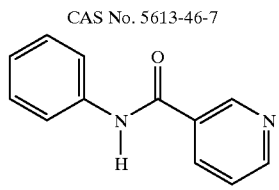
CAS No. 1752-96-1

In Table I, Ac represents an acyl group.

Suitable termiticides for use in this invention also include compounds of Formula II, below:

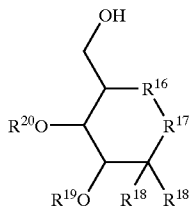

wherein each $R^{16}$ is independently selected from the group consisting of an oxygen atom and $CH_2$. $R^{16}$ is preferably an oxygen atom.

each $R^{17}$ is independently selected from the group consisting of C=O and $CR^{21}(R^{22})$, wherein $R^{21}$ and $R^{22}$ are each independently selected from the group consisting of a hydrogen atom, OH, a halogen atom, $CR^{28}R^{23}{}_2$, and $OR^{24}$, wherein $R^{24}$ is an aromatic group that may optionally be substituted with one or more groups such as $NO_2$. Each $R^{23}$ is independently selected from the group consisting of a halogen atom, a hydrogen atom, a hydrocarbon group, an aromatic group, and an acyl group; with the proviso that at least one $R^{23}$ is a halogen atom. The preferred halogen atom for $R^{23}$ is fluorine. The hydrocarbon group and the aromatic group for $R^{23}$ may optionally be substituted. $R^{28}$ is selected from the group consisting of $R^{23}$ and groups of the formulae:

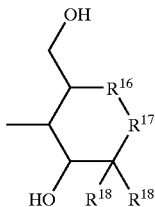 and 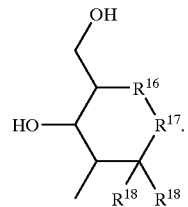

Each $R^{18}$ is independently selected from the group consisting of a hydrogen atom, a halogen atom, and OH. The preferred halogen atom for $R^{18}$ is fluorine.

Each $R^{19}$ and each $R^{20}$ are independently selected from the group consisting of a hydrogen atom, and a group of the formula:

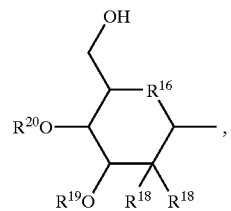

with the proviso that $R^{19}$ and $R^{20}$ are not both the group of the formula

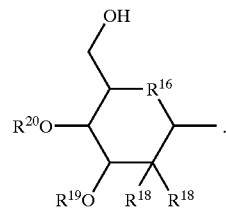

Preferably, $R^{19}$ is a hydrogen atom. Examples of compounds of Formula II are shown below in Table II.

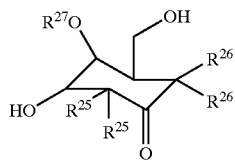 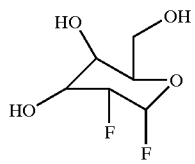

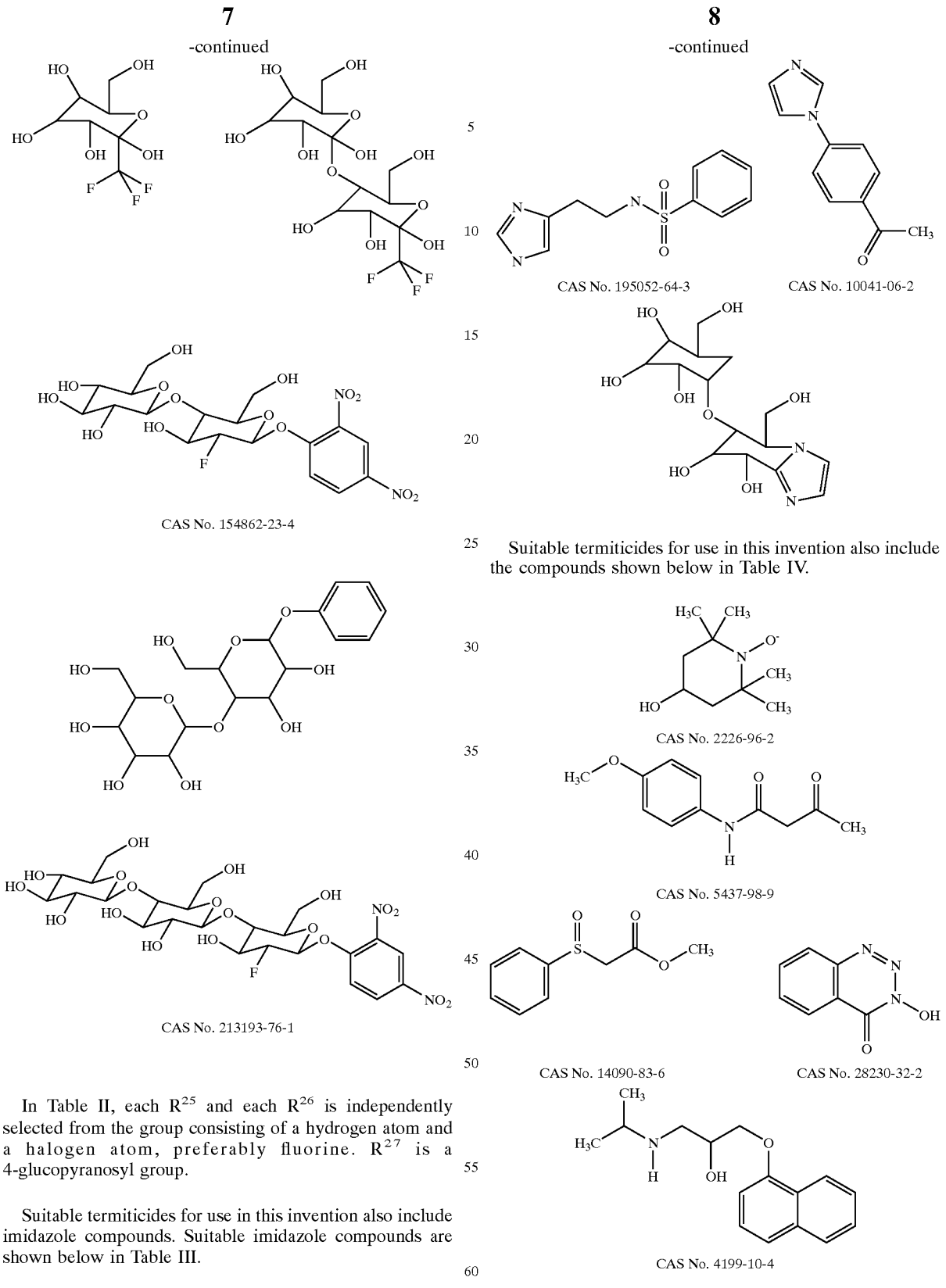

In Table II, each $R^{25}$ and each $R^{26}$ is independently selected from the group consisting of a hydrogen atom and a halogen atom, preferably fluorine. $R^{27}$ is a 4-glucopyranosyl group.

Suitable termiticides for use in this invention also include imidazole compounds. Suitable imidazole compounds are shown below in Table III.

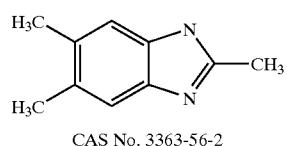

CAS No. 3363-56-2

Suitable termiticides for use in this invention also include the compounds shown below in Table IV.

Other suitable termiticides include n-bromyl succinimide, phenyl-beta-D-glycoside, 4,4'- isopropylidenedicyclohexanol, 2,5,6-trimethylbenzylimidazole, hexachloropalladate compounds, polyphenols, and combinations thereof. Suitable hexachloropalladate compounds include ammonium hexachloropalladate, sodium hexachloropalladate, and combinations thereof. Suitable polyphenols include Aspidosperma quebracho-blanco extract, Cucurbitaceae fruit & green tea extract, and combinations thereof.

The termiticide of this invention can be a single termiticide or a combination of two or more termiticides described above.

The termiticide used in this invention typically comprises a cellulase inhibitor. Termites require digestive cellulases to hydrolyze the cellulose in the wood they ingest as food. The cellulases hydrolyze cellulose to glucose. Without wishing to be bound by theory, it is thought that cellulase inhibitors ingested by a termite prevent one or more of the cellulases in the gut of the termite from digesting cellulose, at least to some degree, e.g., a degree sufficient to kill the termite. Suitable cellulase inhibitors include β-glucosidase inhibitors, endoglucanase inhibitors, exoglucanase inhibitors, and combinations thereof.

Preferred cellulase inhibitors are compounds specific to cellulase, i.e., they do not inhibit or change the action of many proteins other than cellulases. More preferred cellulase inhibitors are compounds that do not inhibit or change the action of proteins found in animals other than termites, particularly humans. Most preferred cellulase inhibitors, for purposes of this invention, are compounds that do not inhibit or change the action of any proteins other than cellulases. Compounds specific to cellulase are preferred for use as the cellulase inhibitors of this invention. Without wishing to be bound by theory, it is thought that compounds specific to cellulases that do not inhibit or change the action of other proteins will be safe (nontoxic) to humans and other mammals. One skilled in the art will recognize that while compounds specific to cellulase are preferred for use in this invention, they are not limiting. Other cellulase inhibitors, which are not necessarily specific to cellulase, are also suitable to use in this invention.

Cellulase is a general term for any of the enzymes that together make-up the cellulase complex. (Most organisms that produce cellulases produce a cellulase complex consisting of a natural enzyme mix of multiple exoglucanases, endoglucanases, and β-glucosidase as well as other enzymes.) Whether a compound is a cellulase inhibitor can be determined without undue experimentation using methods known in the art. Many cellulase enzyme activity assays are available using a variety of substrates (see for example, Methods in Enzymology, Volume 160, Biomass Part A, Cellulose and hemicellulose, ed. W. A. Wood & S. T. Kellogg, Academic Press, NY 1988).

To measure the enzyme activity of any one cellulase, a specific assay and substrate are selected for the specific cellulase of interest (e.g., an appropriate substrate for β-glucosidase is p-nitrophenyl β-1,4-glucopyranoside). Other assays and substrates are more appropriate to measure enzyme activity of the cellulase complex (e.g., an appropriate substrate for the cellulase complex comprising a natural mix of exoglucanases, endoglucanases, and β-glucosidase is cellulose azure).

The enzyme assays are used to establish a rate for cellulase hydrolysis of the substrate in the absence of an inhibitor. Each potential inhibitor is also mixed with the cellulase enzyme and the same assay is performed on the combination of the cellulase and the potential inhibitor. Cellulase inhibition is measured as a reduction in rate of hydrolysis of the substrate, compared to the enzyme rate without inhibitor.

Suitable cellulase inhibitors for use in this invention include, but are not limited to, the compounds shown below in Table V; compounds having the following CAS Numbers 10192-62-8, 19168-23-1, 85803-43-6, 62220-58-0, 21393-76-1; and combinations thereof.

TABLE V

Cellulase Inhibitors

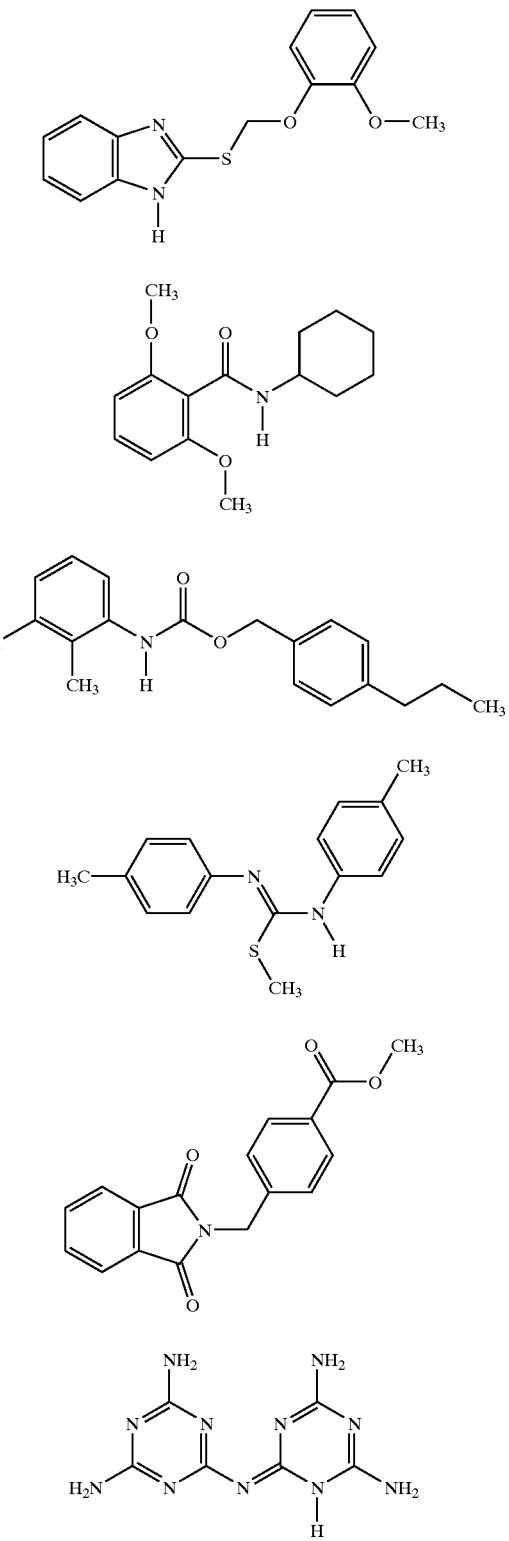

TABLE V-continued

Cellulase Inhibitors

CAS No. 80-04-6

TABLE V-continued
Cellulase Inhibitors
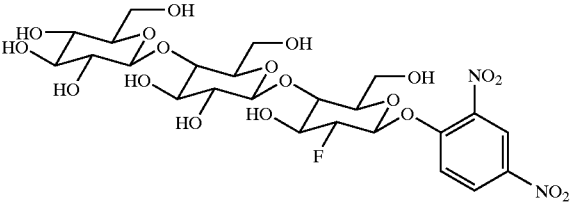
CAS No. 213193-76-1
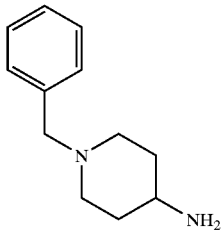
CAS No. 50541-93-0
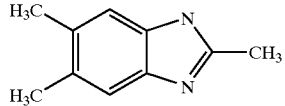
CAS No. 3363-56-2
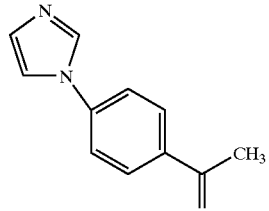
CAS No. 10041-06-2
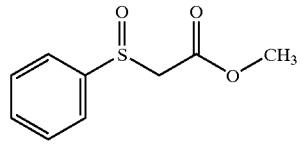
CAS No. 14090-83-6
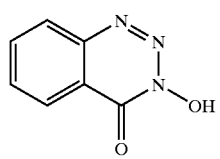
CAS No. 28230-32-2
TABLE V-continued
Cellulase Inhibitors
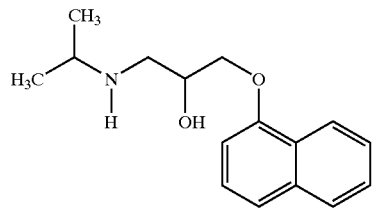
CAS No. 4199-10-4
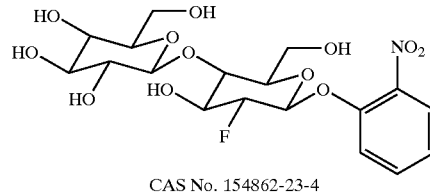
CAS No. 154862-23-4
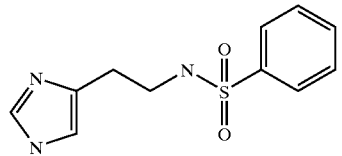
CAS No. 195052-64-3
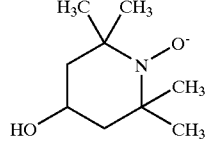
CAS No: 2226-96-2
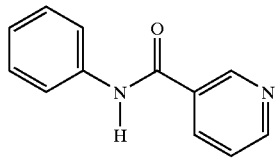
CAS No. 1751-96-1
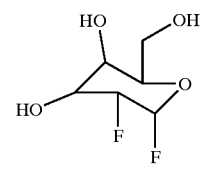
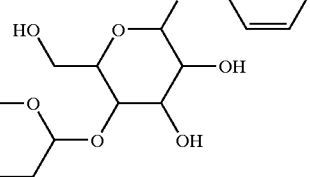

In an alternative embodiment of the invention, the termiticide further comprises one or more slow acting toxicants. Suitable slow acting toxicants include amidinohydroazones, amylase inhibitors, antiprotozoals, barium compounds, biological control agents, boron compounds, chitin synthesis inhibitors, azadirachtin, fluoroalkylsulfonamides, glucose antimetabolites, hexokinase and glucokinase inhibitors, imidacloprid, juvenile hormones and juvenile hormone mimics and juvenile hormone analogs, macrolide antibiotics, metal compounds, combinations thereof, and others.

Suitable amidinohydroazones include avermectin, hydramethylnon, silafluofen, and combinations thereof.

Suitable amylase inhibitors include acarbose, cyclohexaamylose, trestatin, and combinations thereof.

Suitable antiprotozoals include toxins to termites' gut dwelling cellulase producing protozoa. Suitable antiprotozoals include 5,7-diiodo-8-hydroxyquinoline (iodoquinol), di-(4-aminophenylsulfone) (dapsone), 1-methyl-4-diiodomethylsulfonylbenzene (diiodomethyl-paratolylsulfone), and combinations thereof.

Suitable barium compounds include barium metaborate monohydrate.

Suitable biological control agents include fungi such as *Metarhizium anisopliae, Aspergillus flavus*, and *Beauveria bassiania*; nematodes such as *Neoplectana carpocapsae*; insect viruses; bacteria such as *Bacillus thuringiensis* and *Serratia marcescens*; and combinations thereof.

Suitable boron compounds include boric acid, disodium octaborate tetrahydrate, zinc borate, ulexite, colemanite, calcium boride, and combinations thereof.

Suitable chitin synthesis inhibitors include hexaflumuron, flufenoxuron, lufenuron, and diflubenzuron (Dimilin), and combinations thereof.

Suitable fluoroalkylsulfonamides include sulfluramid.

Suitable glucose antimetabolites include 5-thio-D-glucose; 2-deoxy-D-glucose; nojirimycin; nojirimycin bisulfide; 1-deoxynojirimycin; and p-nitrophenyl-$\alpha$-D-glucoside in mono-, di-, or polymer form, and combinations thereof.

Suitable hexokinase and glucokinase inhibitors include lauric acid, myristic acid, glucosamine, 6-amino-6-deoxy-D-glucose, N-acetylglucosamine, and combinations thereof.

Suitable juvenile hormones and juvenile hormone mimics or analogs include fenoxycarb, methoprene, hydroprene, triprene, fumesinic acid ethyl and alkoxy derivatives, pyriproxyfen (Nylar), and combinations thereof.

Suitable macrolide antibiotics include abamectin, milbemycin, spinosyn A, spinosyn D, and combinations thereof.

Suitable metal compounds are molybdenum or tungsten compounds. Suitable molybdenum compounds include $MoO_3$, $H_2MoO_4$, $CaMoO_4$, $Na_2MoO_4$, $FeMoO_4$, and combinations thereof. Suitable tungsten compounds include $Na_2WO_4$.

Suitable slow acting toxicants are disclosed in U.S. Pat. No. 4,504,468; U.S. Pat. No. 4,636,798; U.S. Pat. No. 5,609,879; U.S. Pat. No. 5,637,298; U.S. Pat. No. 5,695,776; U.S. Pat. No. 5,756,114; U.S. Pat. No. 5,778,5961; and U.S. Pat. No. 5,937,571 which are hereby incorporated by reference for the purpose of disclosing suitable slow acting toxicants.

Typically the amount of ingredient a) in the bait matrix is about 0.1 to about 10%. However, the exact amount of ingredient a) in the termiticidal bait matrix will depend on the specific component or components in the termiticide, e.g., the potency of each component. The termiticides of this invention are preferably slow acting, i.e., they do not kill the termite immediately after ingestion. Without wishing to be bound by theory, it is thought that if foraging termites are killed too quickly after they ingest the termiticide, they will not have time to make repeated visits to the source of the termiticide and communicate the source to other termites or to transport it back to the colony.

Ingredient b) is a cellulose containing material. Examples include wood, charred wood, decayed wood, sawdust, pulp, paper, cotton linter, cellulose ethers, and combinations thereof. Suitable types of wood include basswood, aspen, cottonwood, paper birch, soft maple, yellow poplar, beech, pecan, hard maple, persimmon, pine, fir, spruce, and combinations thereof. Suitable types of paper include 100% virgin paper, recycled paper, a combination of virgin and recycled paper, paperboard, cardboard, and combinations thereof. Paper may be bleached, typically with one or more solutions, e.g., aqueous solutions, of bleaching chemicals. Paper can optionally be textured or roughened and may optionally comprise a plurality of plies. Suitable cellulose ethers include methylcellulose, hydroxypropylmethylcellulose, hydroxybutylmethylcellulose (commercially available as METHOCEL® from the Dow Chemical Company), and combinations thereof. Typically the amount of ingredient b) in the bait matrix is about 5 to about 50%.

Ingredient c) is water. The amount of water in the bait matrix is typically about 5 to about 50%.

Ingredient d) is one or more optional ingredients selected from the group consisting of attractants, defoamers, dextrin, dispersing agents, extenders, feeding stimulants, flavors, grain powder, moisture adjusting means, nitrogen sources, nutrients, penetrants, stabilizers, sugars, surface active agents, suspending agents, synergists, vegetable oils, and combinations thereof. Typically the amount of ingredient d) in the bait matrix is about 1 to about 10%.

Suitable attractants for ingredient d) include pheromones, 2-naphthalene-methanol, naphthalene, 2-phenoxyethanol, steroid derivatives, cow dung, camphor, thujene, linalol, cadinene, turpentine oil, borneol, methylanisol, cinnamyl alcohol, isosafrole, steroid derivatives, and combinations thereof.

Suitable nutrients for ingredient d) include agar or a mixture of agar and a wet gel.

Suitable moisture adjusting means for ingredient d) include humectants.

Suitable feeding stimulants for ingredient d) include ergosterol, fermented milk, p-hydroquinone, hydroxyphenyl-$\beta$-D-glycopyranoside, catechol, resorcinol, fluoroglucinol, 4-methoxyphenol, 1,4-dimethoxybenzene, 4-phenoxyphenol, phenylhydroquinone, 4-benzyloxyphenol, quinhydrone, and combinations thereof. Hydroquinone is preferred.

Suitable syngergists for ingredient d) include butoxyethoxyethoxymethylenedioxypropyltoluene, octachlorodipropyl ether, isobornylthiocyanato acetate, ethylhexylbicycloheptenedicarboxyimide, and combinations thereof.

Suitable stabilizers for ingredient d) include butylated hydroxyanisole, butylated hydroxytoluene, tocophereols, and combinations thereof.

Suitable nitrogen sources for ingredient d) include uric acid, amino acids, peptides, proteins, and combinations thereof.

In an alternative embodiment of the invention, a nontermiticidal bait matrix can be prepared. The nontermiticidal bait matrix comprises ingredient b) described above. The nontermiticidal bait matrix optionally further comprises ingredients c) or d), or both, described above. Typically, the nontermiticidal bait matrix comprises ingredients b) and c). The nontermiticidal bait matrix does not contain a termiticide.

The exact composition of the bait matrices described above, i.e., amounts of each ingredient and selection of ingredients, may depend on the type of termites being targeted. For example, different types of termites may prefer different types of wood. Without wishing to be bound by theory, it is thought that hardness of the wood is one factor contributing to termites' preferences. Different types of termites also may prefer different feeding stimulants. Therefore, the bait matrix can be targeted to kill different types of termites by selection of cellulose containing materials, feeding stimulants, termiticides, and optional ingredients in the bait matrix.

The bait matrix may have a variety of forms. The bait matrix may be a solid or a fluid. The bait matrix can be, for example, a solid piece of wood coated with or impregnated with ingredients a), c), and optionally d). In one embodiment of the invention, the bait matrix is a solid b) cellulose containing material coated or impregnated with ingredients a), c) and optionally d), wherein the solid b) has one or more grooves therein. For example, the solid b) may be a rectangular block having a plurality of grooves cut along one or more sides of the rectangular block. The length of each groove preferably extends from one end of the rectangular block to the other end. Preferably, the width of each groove is about 1/32 inch to about 1 inch, preferably about 1/8 inch. In this embodiment of the invention, the bait matrix has a form similar to that in U.S. Pat. No. 5,695,776, which is hereby incorporated by reference.

The bait matrix can be used alone or in conjunction with a bait station. When the bait matrix is used alone, it is preferably in the form of a solid. The bait matrix may be placed in or near a locus of potential or known termite activity. In an alternative embodiment of the invention, the bait matrix is used in a bait station.

Bait Station

This invention further relates to bait stations and kits including bait matrices and bait stations. A suitable bait station comprises a housing adapted to receive one or more of the bait matrices described above. The housing has at least one opening sized to permit termites to pass through the opening so that termites can gain access to the bait matrix from a location outside the housing. Typically, the housing has a plurality of openings. The housing is adapted to be installed in or near a locus of potential or known termite activity.

In an alternative embodiment of the invention the bait station further comprises a lid removably attached to an open end of the housing. This will allow for removal or replacement, or both, of the bait matrix when it is exhausted or partially exhausted. The bait station may further comprise locking means attaching the lid to the housing, for example, to prevent children from opening the bait station while it is in use.

The bait station may further comprise a removable receptacle for holding the bait matrix inside the housing, wherein the receptacle has at least one opening, typically a plurality of openings, sized to permit termites to pass through the opening. The openings in the housing and the receptacle are typically at least partially aligned to allow termites access to the bait matrix when the receptacle is installed inside the housing.

In one embodiment of the invention, wherein the bait station will be installed in-ground, the bait station has dimensions suitable for installation using manual digging implements.

The bait station may comprise any suitable materials of construction, for example polyvinyl chloride or a thermoplastic material that is opaque, translucent, or transparent. In one embodiment of the invention at least part of the bait station, e.g., the lid, is at least partially transparent so that termite activity can be monitored without moving or opening the housing. In an alternative embodiment of the invention, at least part of the bait station, e.g., the lid, is colored to match its surroundings when the bait station is installed.

An example of a suitable bait station is shown in FIG. 1. The bait station 100 comprises a housing 101 adapted to receive a bait matrix (not shown). The housing has openings 102 sized to permit termites to pass through to gain access to the bait matrix from a location outside the housing 101. The housing 101 has a metal tip 103 on one end and a strike plate 104 on the other end. The metal tip 103 and strike plate 104 allow the bait station 100 to be driven into the ground by pounding with, for example, a hammer or mallet.

Figure 2:
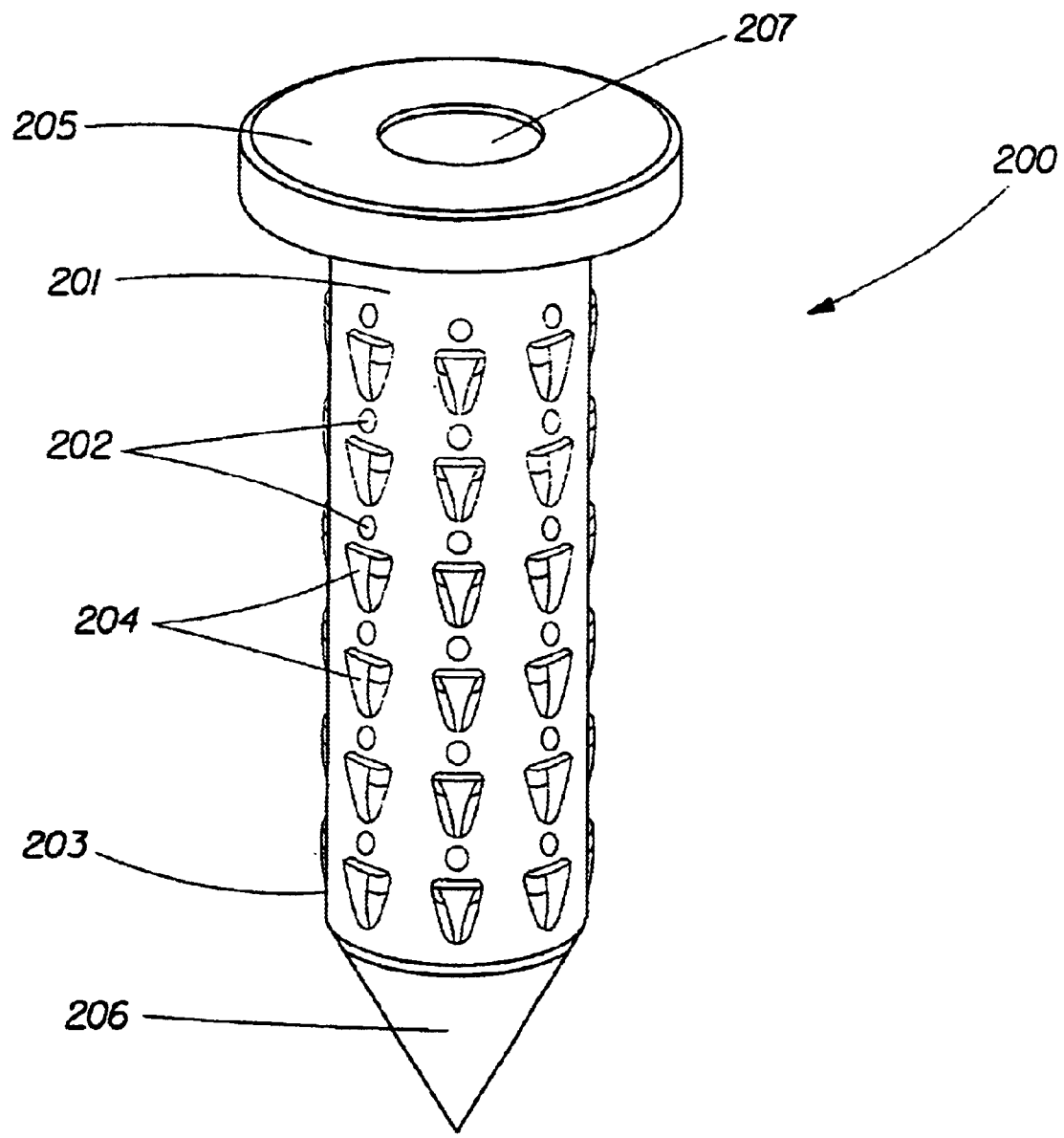
FIG. 2 is a bait station according to this invention.

Another bait station is shown in FIG. 2. The bait station 200 comprises a housing 201 adapted to receive a bait matrix (not shown). The housing 201 has openings 202 sized to permit termites to pass through to gain access to the bait matrix from a location outside the housing 201. The outside surface 203 of the housing 201 has a ridge 204 under each opening 202. Without wishing to be bound by theory it is thought that the ridges may prevent soil from plugging the openings 202 when the bait station 200 is installed in-ground. The housing 201 has a plate 205 at the top and a tip 206 at the bottom. The tip 206 can be, for example, a metal tip installed over the end of a plastic housing 201, or the tip 206 hard plastic that is part of the housing 201. The plate 205 may be struck or pushed to install the bait station in-ground. The plate 205 has an opening 207. A bait matrix can be installed in the housing 201 through the opening 207.

Figure 3:
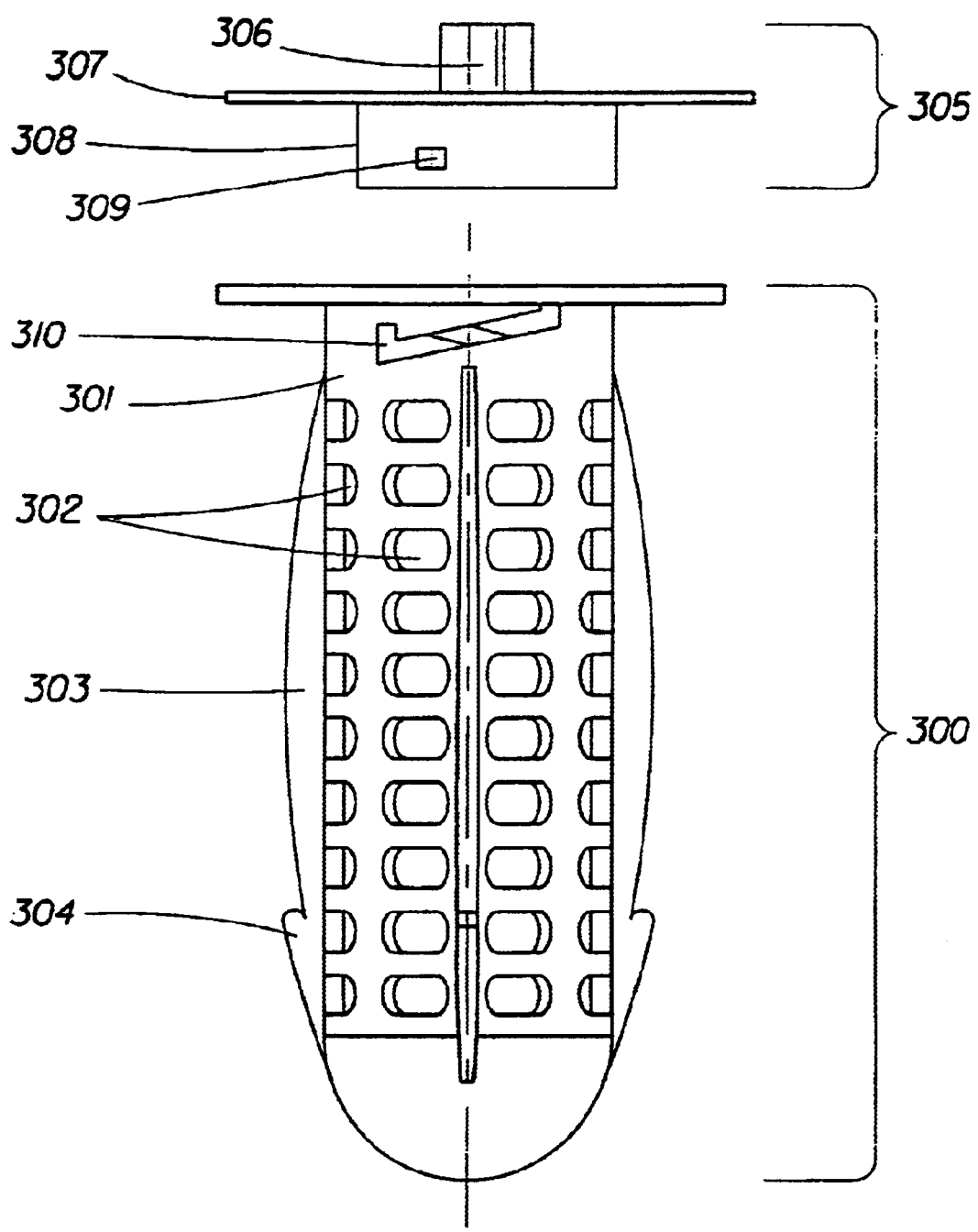
FIG. 3 is a bait station according to this invention.

Another bait station is shown in FIG. 3. The bait station 300 comprises a housing 301 adapted to receive a bait matrix (not shown). The housing 301 has openings 302 sized to permit termites to pass through to gain access to the bait matrix from a location outside the housing 301. The housing 301 has vertical ribs 303 to prevent the bait station 300 from spinning after installation. Each rib 303 has a hook 304 to prevent the bait station 300 from being too easily pulled out of the ground after installation. The bait station 300 further comprises a removable lid 305. The lid 305 comprises a handle 306 removably attached to a plate 307. The plate has an insert 308 opposite the handle 306. The insert 308 has a protruding notch 309 that fits into a groove 310 in the housing 301. When the lid 305 is pushed onto the housing 301, the protruding notch 309 fits into the groove 310. The lid 305 is twisted so that the protruding notch 309 rotates following the groove 310 to a locking position. The handle 306 is typically removed after the lid 305 is placed on the housing.

Figure 4A:
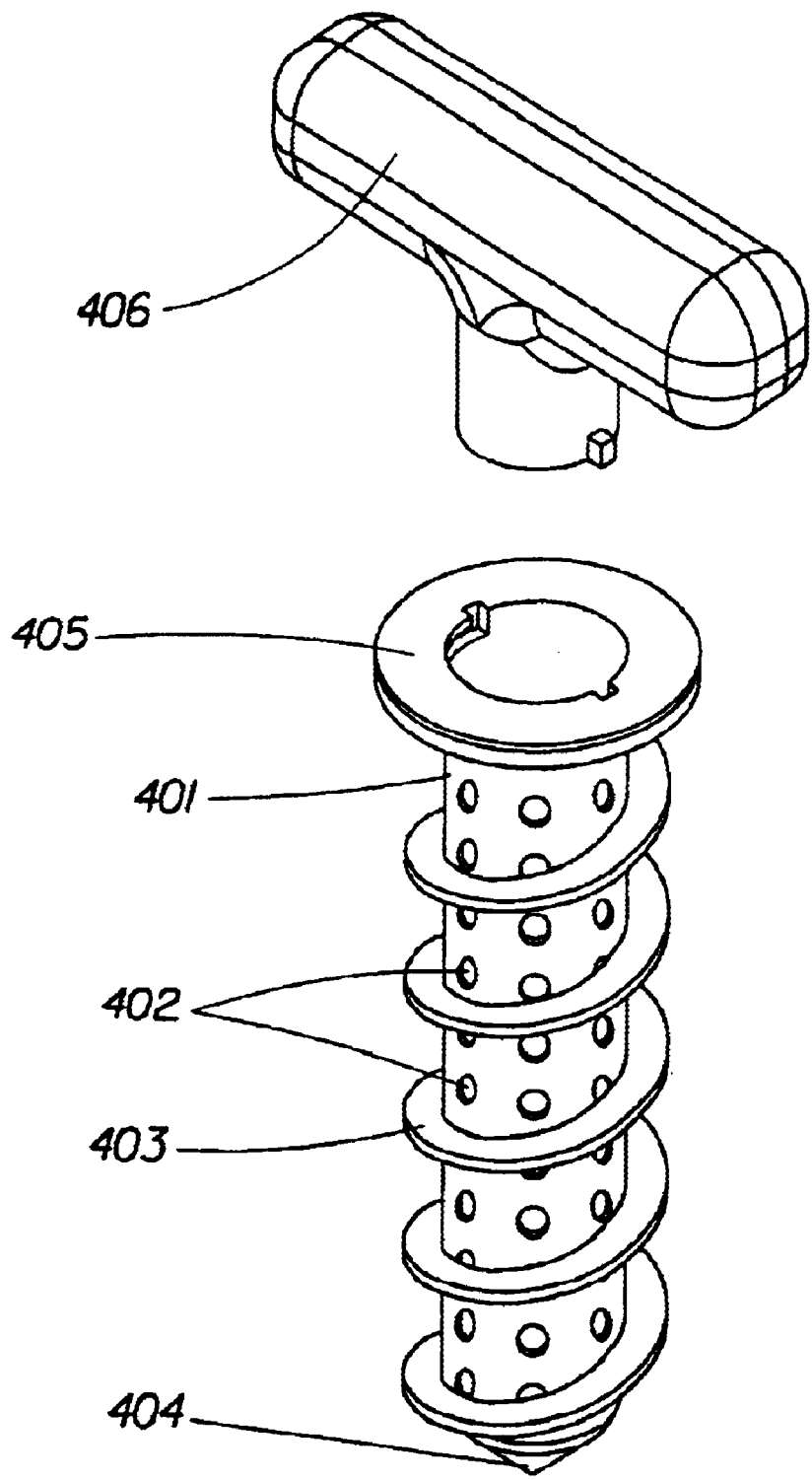
FIG. 4a is a bait station according to this invention.
Figure 4B:
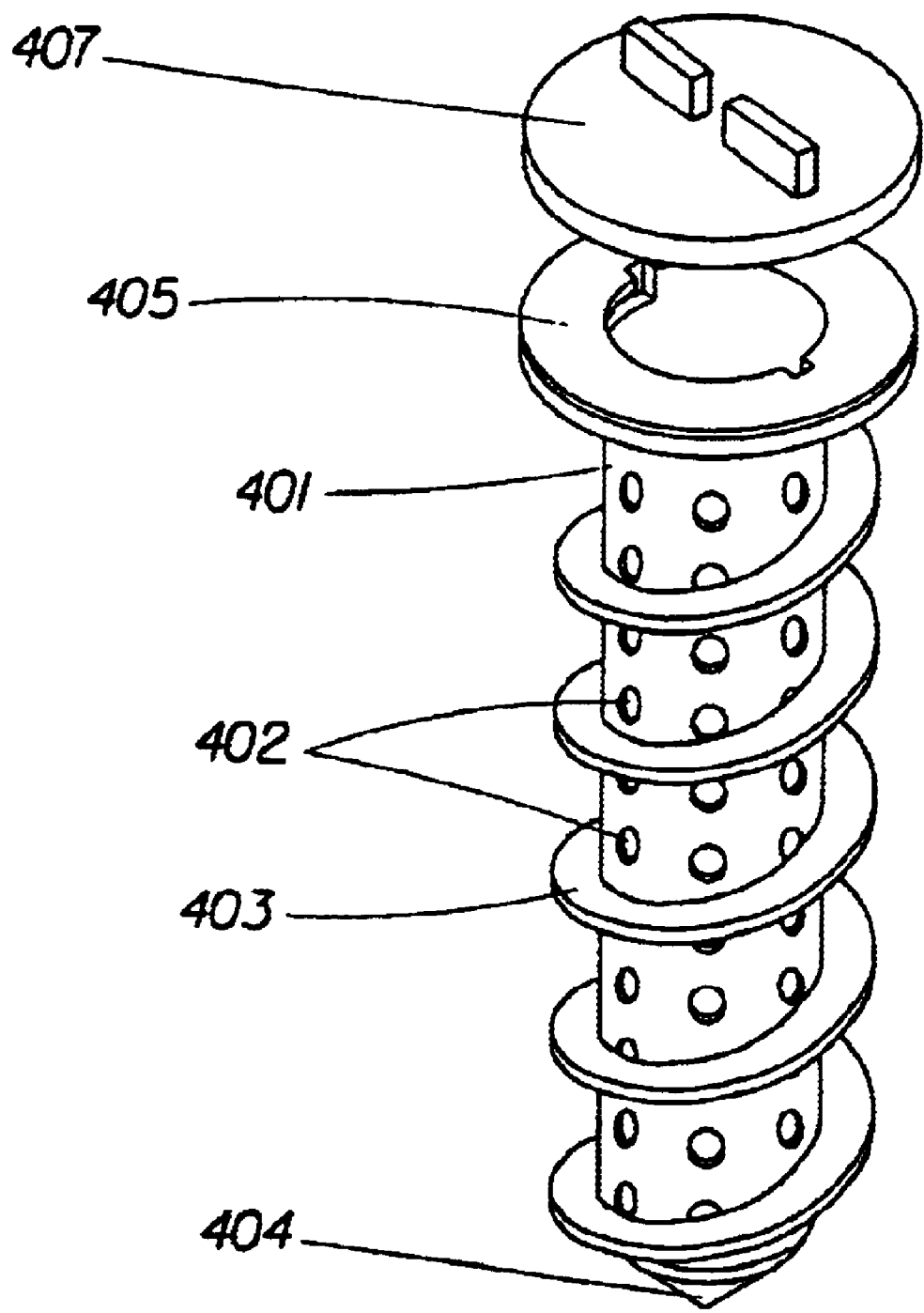
FIG. 4b is a bait station according to this invention.

FIGS. 4a and 4b show a bait station 400 according to an alternative embodiment of this invention. The bait station 400 comprises a housing 401 adapted to receive a bait matrix (not shown). The housing 401 has openings 402 sized to permit termites to pass through to gain access to the bait matrix from a location outside the housing 401. The housing 401 has threads 403 for allowing the bait station 400 to be screwed into the ground. The housing 401 has a pointed tip 404 at the bottom and a flange 405 at the top. The flange 405 is adapted to receive a removable handle 406 (FIG. 4a) that can be used to manually screw the bait station 400 into the ground. After the bait station 400 is screwed into the ground, the handle 406 can be removed and replaced with a lid 407 (FIG. 4b).

In an alternative embodiment of the invention, the bait matrices described above can be used in bait stations that are known in the art. For example, suitable bait stations for use with the bait matrices are disclosed in U.S. Pat. No. 5,695,776; U.S. Pat. No. 5,901,496; U.S. Pat. No. 5,921,018; U.S. Pat. No. 5,927,001; U.S. Pat. No. 5,937,571; U.S. Pat. No. 5,950,356; U.S. Pat. No. 5,899,018; U.S. Pat. No. 6,003,266; U.S. Pat. No. 6,016,625; U.S. Pat. No. 6,058,241; U.S. Pat. No. 6,065,241; U.S. Pat. No. 6,071,529; and U.S. Pat. No. 6,079,150, all of which are hereby incorporated by reference. Other suitable bait stations for use with the bait matrix of this invention are disclosed in WO 00/19816.

Kits

This invention further relates to a kit for eliminating a termite colony. The kit comprises:

i) a termiticidal bait matrix as described above, and ii) a bait station as described above for containing the termiticidal bait matrix.

The kit may further comprise: iii) a nontermiticidal bait matrix, as described above. The nontermiticidal bait matrix can be installed in the bait station and monitored to determine whether termites are present. If termites are detected, the termiticidal bait matrix can be installed in addition to, or in place of, the nontermiticidal bait matrix.

The kit may further comprise: iv) a device for installing the bait station in or near the locus of potential or known termite activity. When the device will be installed in-ground, a variety of devices may be used. Conventional devices, such as manual digging implements used to plant bulbs may be sufficient e.g., a spade, shovel, or manual auger can be used. Other conventional devices such as an auger with an electric drill can be used. Preferably, the device for installing a bait-station in-ground creates a hole having about the same dimensions as the bait station is used.

Figure 5:
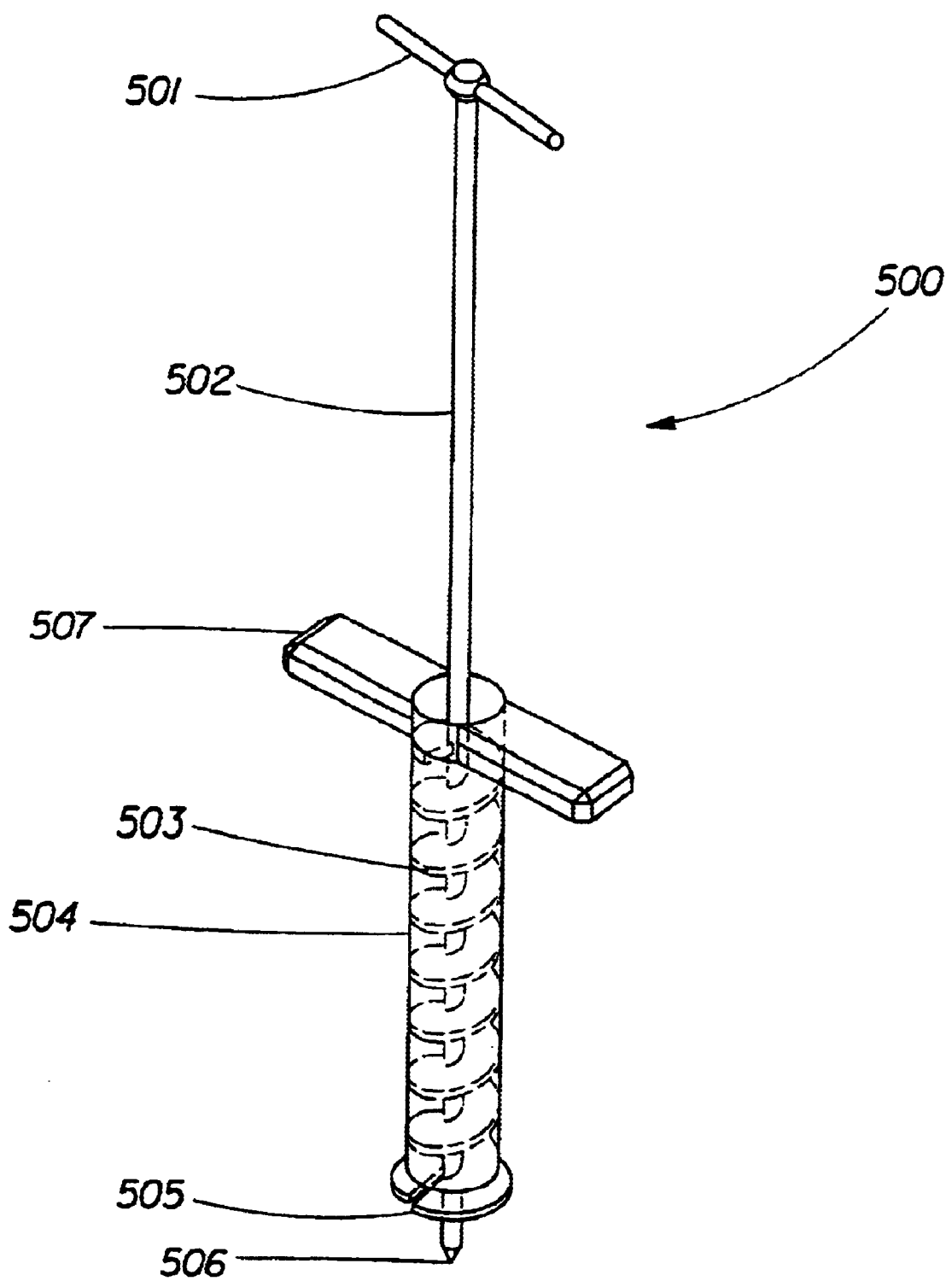
FIG. 5 is a device for installing a bait station according to this invention.

FIG. 5 shows a device 500 for installing a bait station in-ground. The device 500 comprises a handle 501 that can be manually turned by a consumer. The handle 501 is attached to a shaft 502 having a screw 503 inside a pipe 504, with a blade 505 that is slightly larger in diameter than the pipe 504 at the end of the screw 503. The pipe 504 allows soil to be pushed out of a hole bored by the blade 505 without disturbing the soil surrounding the hole. The shaft 502 ends at a point 506 below the blade 505. A foot brace 507 is attached to the end of the pipe 504 opposite the blade 505. The foot brace 507 can be used to exert downward pressure as the handle 501 is twisted.

Figure 6A:
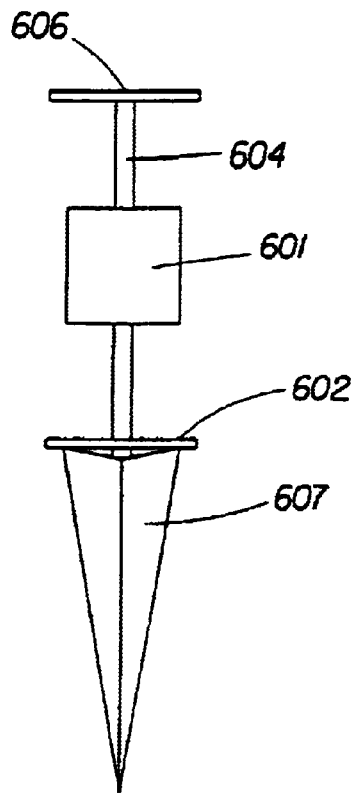
FIG. 6a is a closed view of a device for installing a bait station according to this invention.

FIG. 6a shows a device 600 for installing a bait station in-ground according to an alternative embodiment of this invention. The device 600 is in its closed position. The device 600 comprises a sliding hammer 601 that slides along a rod 604 having a top surface 606 and a bottom surface 602. The sliding hammer 601 is used to strike the bottom surface 602. Attached to the bottom surface 602 are a wedge (not shown) and at least three wings 607 surrounding the wedge 605.

Figure 6C:
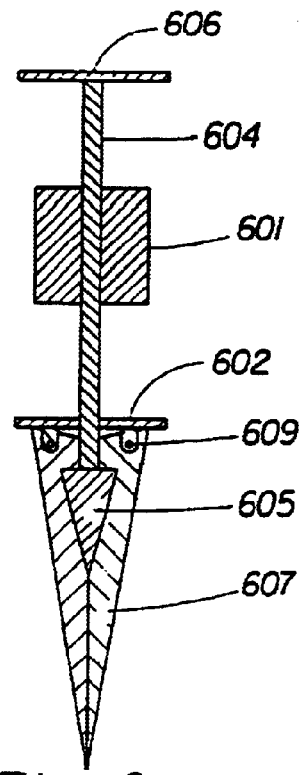
FIG. 6c is a cross section of a device for installing a bait station according to this invention.
Figure 6B:
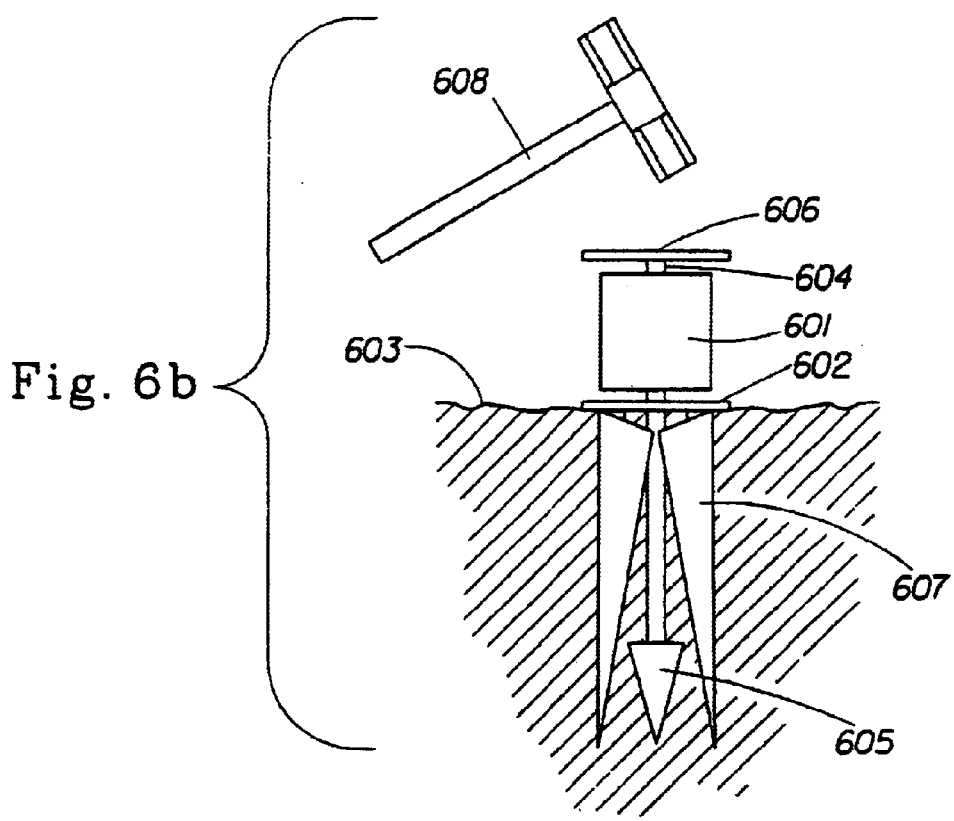
FIG. 6b is an open view of a device for installing a bait station according to this invention.

FIG. 6b shows the device 600 in its open position. The sliding hammer 601 drives the wedge 605 and wings 607 into the ground until the bottom surface 602 reaches ground level 603. After the bottom surface 602 reaches ground level 603, the top surface 606 is struck, for example, with a hammer or mallet 608, thereby driving the wedge 605 further into the ground and spreading the wings 607.

FIG. 6c shows a cross section of the device 600 in FIG. 6a. The device 600 comprises a sliding hammer 601 that slides along a rod 604 having a top surface 606 and a bottom surface 602. The sliding hammer 601 is used to strike the bottom surface 602. Attached to the surface are a wedge 605 and at least three wings 607 surrounding the wedge 605. The wings 607 are attached to the bottom surface 602 by hinges 609.

Figure 7:
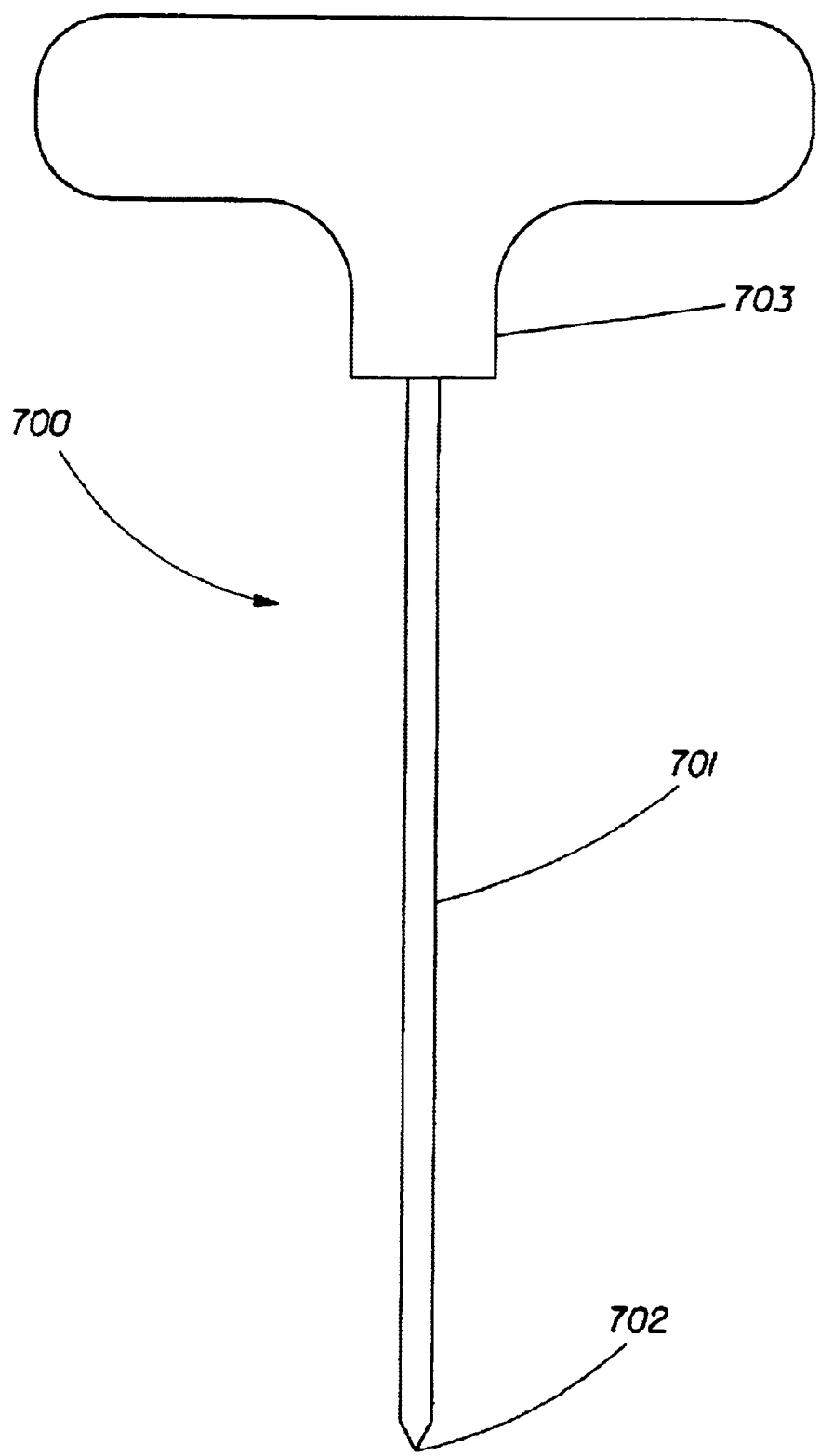
FIG. 7 is a probe for use in a kit according to this invention.

The kit may further comprise: v) a probe for determining whether obstructions are present in-ground where the bait station will be installed. This probe can be, for example, a thin rod that can be manually pushed into the ground where a consumer wishes to install a bait station prior to pounding a bait station into the ground or boring a hole in which the bait station will be installed. The probe is used to determine a suitable location for the bait station without boring a large hole (i.e., large enough to hold the bait station). FIG. 7 shows a probe for use in this invention. The probe 700 comprises a thin rod 701 with a pointed tip 702 and a handle 703 for manually pressing the probe 700 into the ground.

The kit may further comprise: vi) information, instructions, or both, for using the kit. The information, instructions, or both, typically comprise words, pictures, videotapes, DVDs, or combinations thereof describing how to install and/or use the bait station, any optional devices for determining whether obstructions are present in-ground, and any optional devices for installing the bait station. Preferably, the information, instructions, or both, describe how to install and replace the bait matrices (termiticidal and nontermiticidal, if any).

The bait stations in the kits of this invention can be installed in or near a locus of potential or known termite activity. The locus may be above-ground, in-ground, or on-ground. In one embodiment of the invention, the bait station can be installed by attaching it to a structure to be protected. In an alternative embodiment of the invention, the bait station is installed in-ground by partially or completely burying the bait station, e.g., to control subterranean termites.

A bait station installed in-ground is typically buried in a hole about the same size and shape as the bait station. It is preferable not to disturb the surrounding soil. Therefore, devices that bore holes about the same size and shape as the bait station may be used for installing the bait stations.

Figure 8:
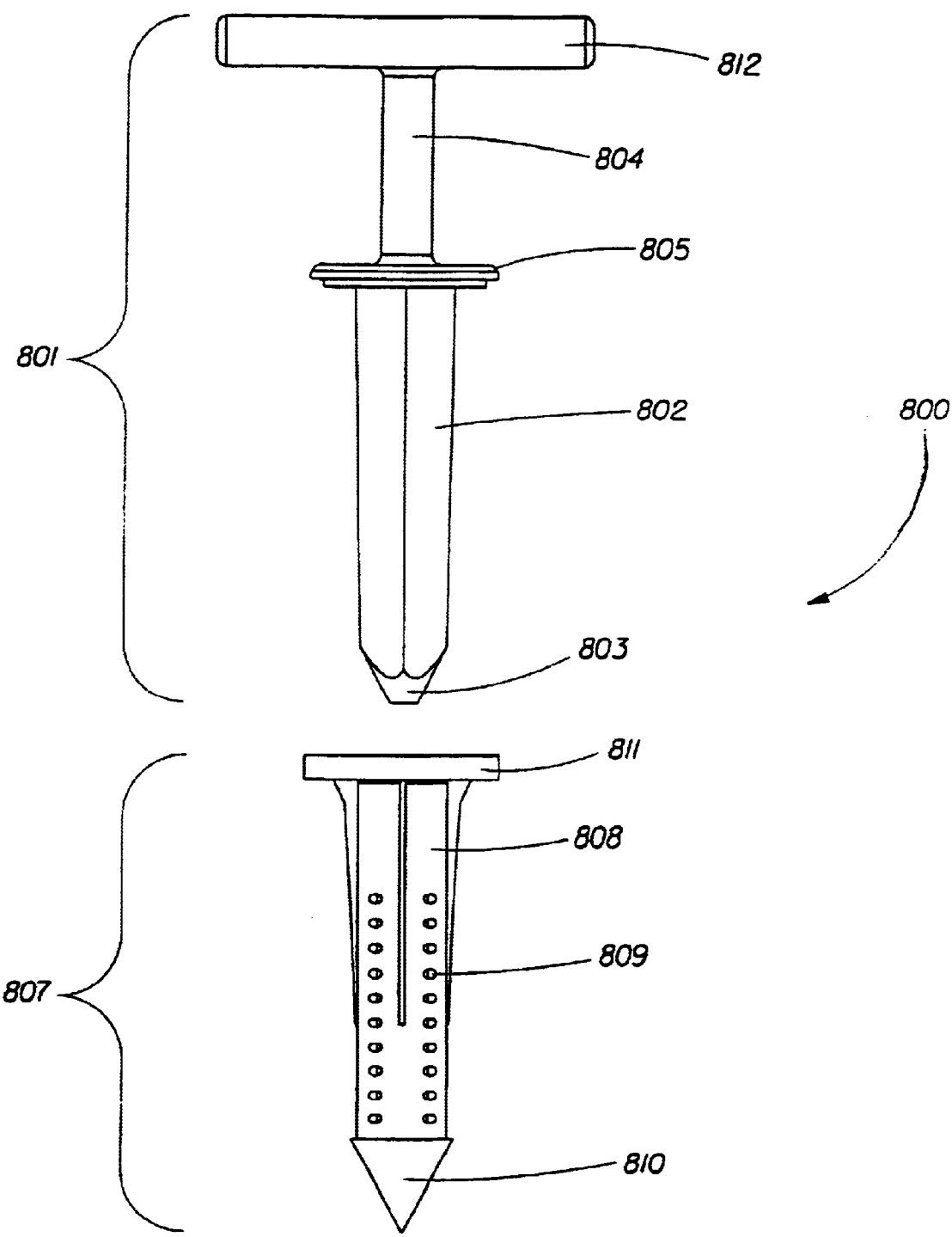
FIG. 8 is a kit according to this invention.

FIG. 8 shows components of a kit 800 according to one embodiment of this invention. A bait station installation device 801 comprising a metal component 802 having a point 803 at one end and a handle 804 at the other can be used to install a bait station 807. In one embodiment of the invention, the device 801 is used manually to bore a hole about the same size and shape as the bait station 807. The device 801 can be tapped into the ground using, for example, a hammer or mallet. The device 801 is driven to a depth up to the flange 805 below the handle 804. The device 801 may then be twisted to slightly loosen the soil further to make inserting the bait station 807 as effortless as possible. After the hole is bored, the device 801 can be inserted into the bait station 807 and used to tap or hammer the bait station into the hole. After the bait station 807 is installed in the hole, the device 801 is removed and a bait matrix (not shown) can be inserted into the housing 808 of the bait station 807. The housing 808 comprises a plurality of holes 809 sized to permit termites to gain entrance to the bait matrix from a location outside the housing 808. The bait station 807 further comprises a pointed tip 810 at the bottom for insertion into the hole and a top flange 811 for receiving the flange 805 of device 801. The device 801 has a raised area 812 for indicating where to tap the device with the hammer or mallet on top of the handle 804.

In an alternative embodiment of the invention, the device 801 is installed in the bait station 807 and the device 801 is struck with a hammer or mallet on the raised area 812 to install the bait station 807 in the ground, without first boring a hole. In this embodiment, the point 803 of the device 801 directs the force from striking to the tip 810 of the bait station 807. In this embodiment, the tip 810 is preferably made of metal.

Methods of Use

This invention further relates to a method for eliminating a termite colony comprising: I) installing in or near a locus of termite activity at least one bait station, wherein the bait station contains a termiticidal bait matrix as described above. The number of bait stations installed in step I) will depend on various factors such as the size of the structure to be protected. Typically, the bait station is installed about 4 to about 6 feet from the structure to be protected. Typically, bait stations are installed about 10 to about 20 feet from each other in a perimeter around the structure. One skilled in the art would be able to determine the appropriate number of bait stations without undue experimentation.

The bait station can be installed by, for example, attaching it to a structure, placing it on the ground, or by burying it partially or completely in-ground.

The method for eliminating a termite colony may further comprise: II) adding more termiticidal bait matrix when the termiticidal bait matrix is exhausted or partially exhausted. Preferably, more termiticidal bait matrix is added about every 1 to about every 3 weeks, more preferably about every 2 weeks until no termite activity is observed.

Using this method, a termite colony can be eliminated in about 3 months or less. Typically, the termite colony can be eliminated in about 3 to about 6 weeks.

This invention further relates to a method for controlling termites comprising:

I) monitoring for termite infestation by a process comprising
  A) checking a bait station for signs of termites, wherein the bait station is installed in or near a locus of potential termite activity, and wherein the bait station contains a nontermiticidal bait matrix, and
  B) determining that termites are present; and
II) installing in the bait station a termiticidal bait matrix, as described above.

Typically, the bait station is checked for signs of termites about every 1 to about every 3 months. Signs of termites include the presence of mud tubes, discarded wings, or sawdust in or near the bait station. Typically, the nontermiticidal bait matrix is replaced about every 3 to about every 9 months, more preferably about every 6 months, before it is determined that termites are present.

This method may further comprise: III) adding more termiticidal bait matrix when the termiticidal bait matrix is exhausted or partially exhausted. Typically, more termiticidal bait matrix is added about every 1 to about every 3 weeks, more preferably about every 2 weeks, until no termite activity is observed.

In a preferred embodiment of the invention, the termiticidal bait matrix can be installed in the bait station without moving or disrupting the nontermiticidal bait matrix. Without wishing to be bound by theory, it is thought that moving or disrupting the nontermiticidal bait matrix may cause termites to abandon the bait station.

The bait stations in the termite control devices and kits of this invention can be installed in or near a locus of potential or known termite activity. In one embodiment of the invention, the bait station can be installed by attaching it to a structure to be protected. In a preferred embodiment of the invention, the device is buried, partially or completely in the ground, e.g., to control subterranean termites. "Structure to be protected" includes but is not limited to buildings such as dwellings and commercial buildings, as well as trees, shrubs, and telephone poles.

EXAMPLES

These examples are intended to illustrate the invention to those skilled in the art and should not be interpreted as limiting the scope of the invention set forth in the claims.

Reference Example 1

Enzyme Activity on the Cellulase Complex Assay

This assay, which is used to measure enzyme activity on the cellulase complex employs, Cellazyme T tablets as the substrate. One-half milliliter aliquots of a properly diluted *Trichoderma reesei* cellulase enzyme complex in sodium acetate buffer (25 millimolar pH adjusted to 4.5) are equilibrated with 50 microliters of inhibitor solution (2.819 milligrams/milliliter in dimethylsulfoxide, "DMSO") at 40° C. for 5 minutes in glass test tubes (16×120 millimeters). (In the enzyme-with-no-inhibitor test tubes, a 50 microliter aliquot of DMSO is added to the test tubes in place of the 50 microliter of inhibitor solution.) A Cellazyme T tablet is then added to the solution. The tablet hydrates to form a suspension very rapidly, however the suspension is not stirred. After 10 minutes at 40° C., 10 milliliters of Trizma base solution (2% w/v, Sigma T-1503) are added before vigorous stirring on a vortex mixer to terminate the enzyme reaction. The slurry is allowed to stand at room temperature for 4–5 minutes, stirred again, and centrifuged at 2000 rpm for 10 minutes. The absorbance of the supernatant is measured at 590 nanometers against a substrate/enzyme blank. (The substrate/enzyme blank is prepared and kept at room temperature by adding the Trizma base to the enzyme before addition of the substrate, thereby terminating the enzyme reaction before it can hydrolyze the substrate.)

Cellulase inhibition is measured as a reduction in rate of hydrolysis of the substrate, compared to the enzyme rate without inhibitor.

Reference Example 2

β-Glucosidase Assay

This assay, which is used to measure enzyme activity for β-glucosidases employs p-nitrophenyl β-1,4-glucopyranoside (Sigma N-7006) as the substrate. A 1.7 millimolar substrate solution in MES buffer (0.05 M MES, pH 6.2) is used in the assay. β-glucosidase (Sigma G-4511) is diluted in MES buffer to 0.05 milligrams/milliliter for use in the assay. The potential inhibitors for testing are contained in individual wells of a 96-well microtiter plate at 170 micromolar in DMSO. Some wells contain DMSO alone to serve as the no-inhibitor enzyme only wells.

Using a second 96-well microtiter plate, aliquots of the inhibitors (20 microliters) and enzyme (25 microliters) are mixed with buffer (100 microliters) and allowed to equilibrate at room temperature for 60 minutes. Fifteen minutes into this equilibration, absorbance at 405 nanometers is measured on the microtiter plate containing the mix to obtain blank values. A UV-visible spectrophotometer plate reader is used to measure all 96-wells in one set.

When the 60-minute equilibration is complete, the substrate (25 microliters) is added to each well, the enzyme reactions allowed to run for 30 minutes, and then quenched with of 1 molar $Na_2CO_3$ solution (100 microliters). Absorbance at 405 nanometers is measured on the reaction plate and the final absorbance calculated by subtracting the corresponding blank value.

Cellulase inhibition is measured as a reduction in rate of hydrolysis of the substrate, compared to the enzyme rate without inhibitor.

Reference Example 3

Termiticide Activity

The tests, run in triplicate, are set up in three wells of a 6-well polystyrene microtiter plate (3 wells are empty). Four circles of either 3.2 cm Whatman #1 filter paper (cellulose) for the food controls and tests on compounds, or 3.2 cm Whatman GF/C glass microfibre filters (borosilicate glass) for the no-food controls are stacked in each well. For the food controls, 600 microliters of water are added to each well. For the no-food controls 1200 microliters of water are added to those wells. If the test compounds are water soluble, they are added to the wells in 600 microliters of water to deliver 0.5% compound. Water insoluble test compounds are added to the wells in a solvent in which they are soluble to deliver 0.5% compound, the solvent is evaporated, and 600 microliters of water added per well.

Termiticidal activity for a compound is measured using termites from the genus/specie *Reticulitermes flavipes* or *Coptotermes formosanus*. The termites are added in groups of 20 per well. Every 3–4 days the termites are counted. The number of days until 50% death ($DTD_{50}$) and 100% death for termites is determined. These values for termites in the wells containing test compounds are compared to the food and no-food controls to determine which compounds display termiticidal activity.

Reference Example 4

Termiticide Preference Test

The test is performed in 100 millimeter Petri dishes into which 20 grams of washed sand and 2 milliliters of water are distributed. Six circles (three plain and three treated with the compound of interest) of Whatman #1 filter paper (15 millimeters) are used as food. The treated circles are prepared by pipetting a small volume (approximately 25 microliters) of a solution of the compound in an appropriate solvent onto the filter paper circles, and then evaporating the solvent.

The filter paper circles are arranged in the dish in two rows using an alternating pattern of treated and untreated. One hundred termites are then added to the dish. The test is run for about 7 days to determine if any eating preference is seen between the treated and untreated filter paper circles.

Example 1

Determination of Termiticidal Activity

Various compounds were analyzed by the method of Reference Example 3. The results are in Table VI.

TABLE VI

| Compound/ CAS No. | Structure | $DTD_{50}$ |
|---|---|---|
| Control | Borosilicate Glass | 54 |
| 80-05-7 | 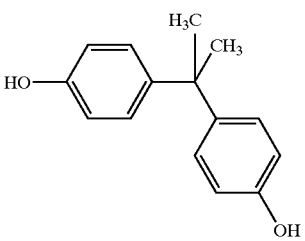 | 42 |
| 80-04-6 | 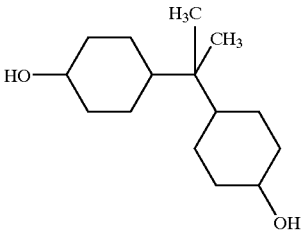 | 62 |

TABLE VI-continued

| Compound/ CAS No. | Structure | DTD$_{50}$ |
|---|---|---|
| 10192-62-8 | 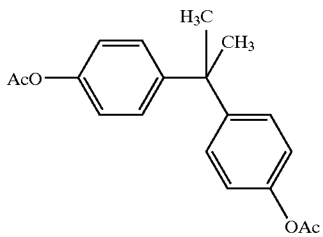 | 70 |
| 154862-23-4 | 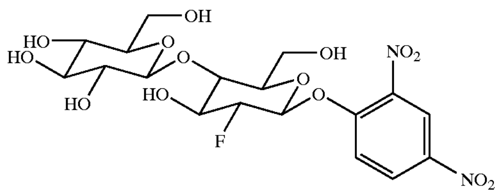 | 66 |
| 213193-76-1 | 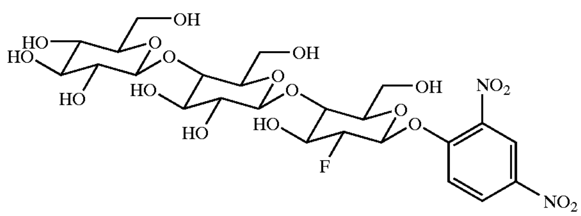 | 60 |
| 50541-93-0 | 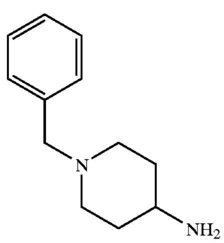 | 59 |
| | | 41 |
| 3363-56-2 | 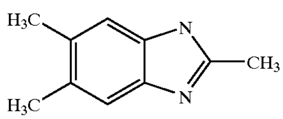 | 63 |
| 195052-64-3 | 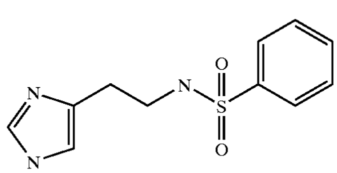 | 48% by day 53 |

TABLE VI-continued
| Compound/CAS No. | Structure | DTD$_{50}$ |
|---|---|---|
| 2226-96-2 | 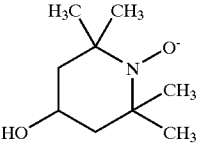 | 32 |
| 1752-96-1 | 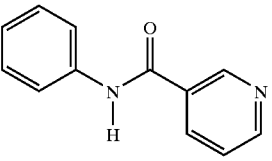 | 80 |
| 5437-98-9 | 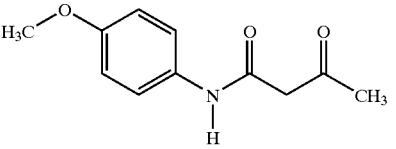 | 31 |
| 10041-06-2 | 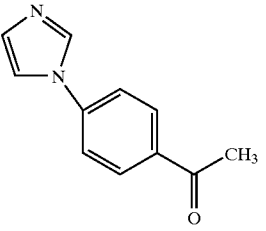 | 35 |
| 14090-83-6 | 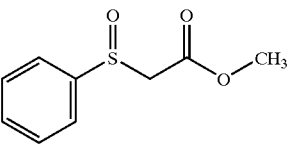 | 35 |
| 28230-32-2 | 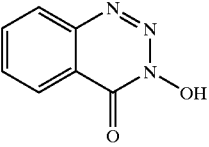 | 80 |
| 5613-46-7 | 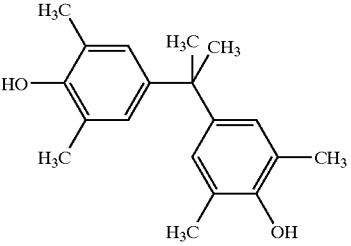 | 42% at day 73 |

TABLE VI-continued

| Compound/CAS No. | Structure | DTD$_{50}$ |
|---|---|---|
| 4199-10-4 | [structure: propranolol-like compound with isopropylamino, hydroxyl, and naphthyloxy groups] | 77 |
| | [structure: difluoro sugar with HO, OH groups] | 33 |
| | [structure: phenyl diglycoside] | 27 |
| | Aspidosperma quebracho-blanco extract | 23 |
| | Cucurbitaceae fruit & green tea extract | 15 |
| 1464-44-4 | Phenyl-beta-D-glycoside | 15 |

Example 1 shows that various compounds can be used as termiticides in this invention. Aspidosperma quebracho-blanco extract, Cucurbitaceae fruit & green tea extract, and Phenyl-beta-D-glycoside are suitable to use as the termiticides in this invention at levels reduced from that in Example 1.

Example 2

Determination of Preference

A compound having CAS No. 80-04-6 is tested according to the method of Reference Example 4, and the compound passes the preference test.

Example 3

Determination of Cellulase Inhibition

Various compounds are tested according to the method of Reference Example 1. Compounds exhibiting cellulase inhibition are shown in Table VII.

TABLE VII

| Compound/CAS No. | Structure |
|---|---|
| 80-04-6 | [structure: bis(4-hydroxycyclohexyl)dimethylmethane] |

TABLE VII-continued
| Compound/ CAS No. | Structure |
|---|---|
| 213193-76-1 | 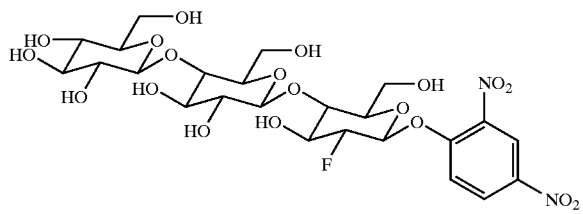 |
| 50541-93-0 | 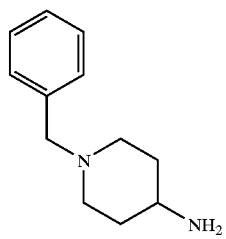 |
| 3363-56-2 | 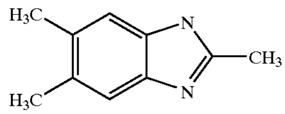 |
| 10041-06-2 | 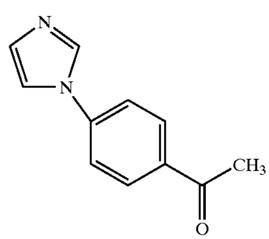 |
| 14090-83-6 | 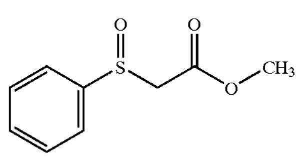 |
| 28230-32-2 | 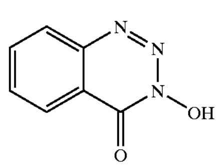 |

TABLE VII-continued

| Compound/ CAS No. | Structure |
|---|---|
| 4199-10-4 | [structure: 1-(isopropylamino)-3-(naphthalen-1-yloxy)propan-2-ol] |

Example 4

Determination of β-Glucosidase Inhibition

Various compounds are tested according to the method of Reference Example 2. Compounds exhibiting β-glucosidase inhibition are shown in Table VIII.

TABLE VIII

| Compound/ CAS No. | Structure |
|---|---|
| 154862-23-4 | [structure] |
| 213193-76-1 | [structure] |
| 50541-93-0 | [structure: 1-benzyl-4-aminopiperidine] |
| 3363-56-2 | [structure: 2,5,6-trimethylbenzimidazole] |
| 195052-64-3 | [structure] |

TABLE VIII-continued

| Compound/CAS No. | Structure |
|---|---|
| 2226-96-2 | 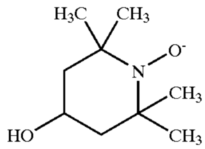 |
| 1752-96-1 | 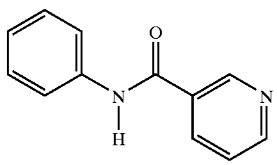 |
| 10041-06-2 | 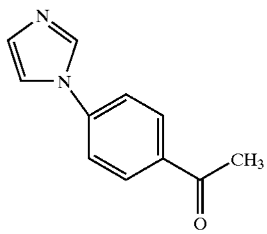 |
| 14090-83-6 | 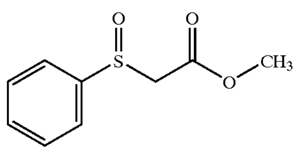 |
| 4199-10-4 | 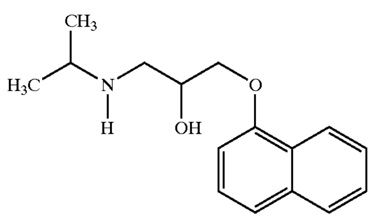 |

Example 5

Synthesis of Compounds of Formula II

Compound I is synthesized in three steps from commercially available pentabenzyl-glucopyranoside. The anomeric hydroxyl of i is first oxidized to ii with the Dess-Martin Periodinane. The resulting lactone is treated with Ruppert's reagent (trifluoromethyl-trimethylsilane) and catalytic fluoride (TBAF) yielding a protected, cyclic hemi-ketal iii at 70% yield. Subsequent treatment with Pearlman's catalyst (Palladium hydroxide, 20% on carbon) provides the free sugar hemi-ketal I in 70% yield.

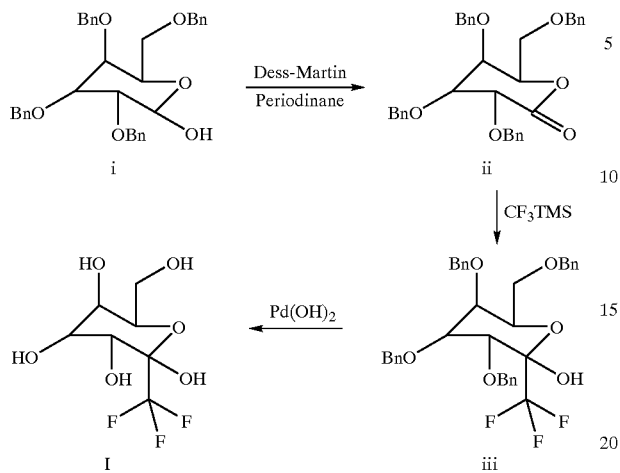

Compound II is obtained similarly. Perbenzylated cellobionolactone, iia is obtained as an intermediate by Br$_2$/water or electrochemical oxidation of cellobiose by methods known in the art; followed by benzylation. One skilled in the art would be able to synthesize compound II without undue experimentation.

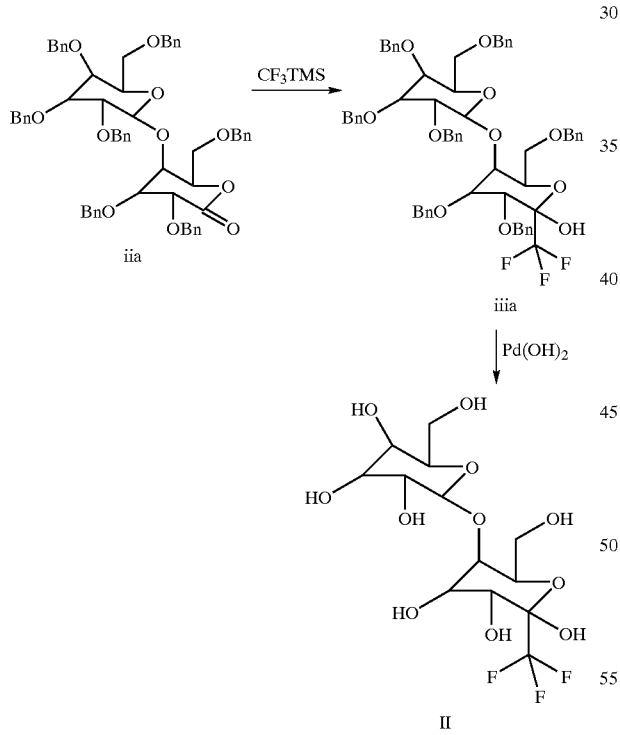

That which is claimed is:

1. A termiticidal bait matrix comprising:

a) a termiticide selected so that the termiticide causes death to about 50 to about 100% of termites within about 24 to about 84 days after the termites begin to ingest the termiticide or the bait matrix comprising the termiticide, where the termicide is a compound of formula

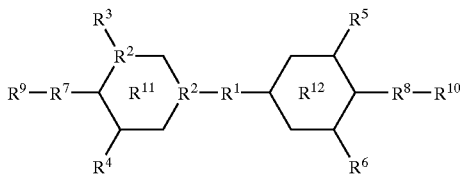

wherein $R^1$ is selected from the group consisting of a bond, a hydrocarbon group, O, and $NR^{14}R^{15}$, wherein $R^{14}$ and $R^{15}$ are each independently selected from the group consisting of a hydrogen atom and a hydrocarbon group;

each $R^2$ is independently selected from the group consisting of CH, a carbon atom, and a heteroatom;

$R^3$, $R^4$, $R^5$, and $R^6$ are each independently selected from the group consisting of hydrogen atoms, hydroxyl groups and methyl groups, and $R^7$ and $R^8$ are each independently selected from the group consisting of hydrogen atoms, oxygen atoms, nitrogen atoms, hydroxyl groups and $NH_2$ groups, wherein (i) when $R^7$ is H, OH or $NH_2$, $R^9$ is absent, and (ii) when $R^8$ is H, OH or $NH_2$, $R^{10}$ is absent;

$R^9$ and $R^{10}$ are each independently selected from the group consisting of hydrocarbon groups of 1 to 6 carbon atoms, alkyl esters of 1 to 6 carbon atoms and amides; and $R^{11}$ and $R^{12}$ are each independently selected from the group consisting of saturated, unsaturated, and aromatic groups, b) a cellulose containing material, and c) water wherein said termiticide is a cellulase inhibitor selected from the group consisting of: β-glucosidase inhibitors, endoglucanase inhibitors, exoglucanase inhibitors and combinations thereof.

2. The bait matrix of claim 1, wherein the termiticide is selected from the group consisting of:

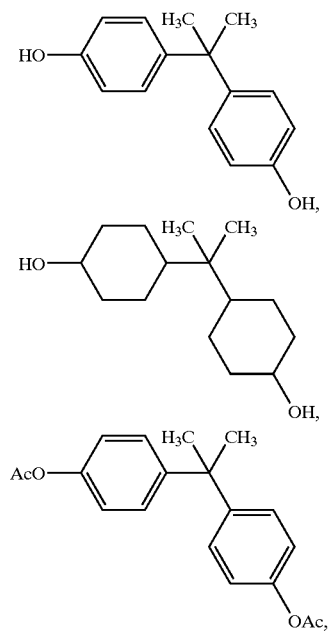

-continued

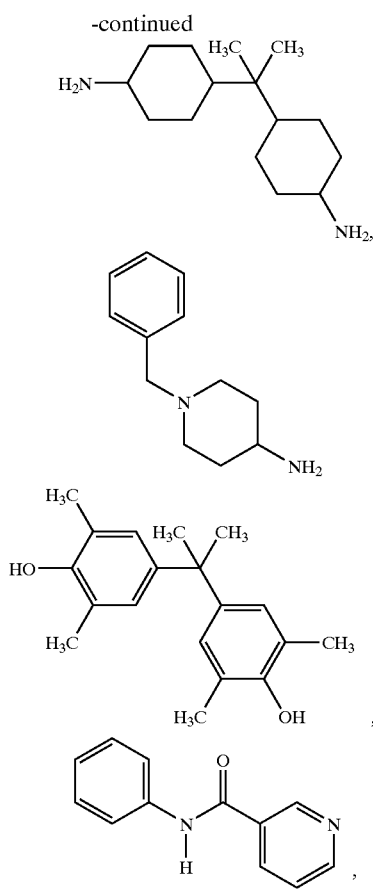

wherein Ac represents an acyl group.

3. The bait matrix of claim 1, wherein the cellulose containing material is selected from the group consisting of wood, charred wood, decayed wood, sawdust, pulp, paper, cotton linter, cellulose ethers, and combinations thereof.

4. The bait matrix of claim 1, further comprising:
d) one or more optional ingredients selected from the group consisting of attractants, defoamers, dextrin, dispersing agents, extenders, feeding stimulants, flavors, grain powder, moisture adjusting means, nitrogen sources, nutrients, penetrants, stabilizers, sugars, surface active agents, suspending agents, synergists, vegetable oils, and combinations thereof.

5. A method for eliminating a termite colony comprising:
I) installing in or near a locus of termite activity at least one bait station, wherein the bait station contains the termiticidal bait matrix of claim 1.

6. The method of claim 5, further comprising: II) adding more termiticidal bait matrix when the termiticidal bait matrix is exhausted or partially exhausted.

7. The method of claim 5, wherein the bait station is installed by attaching it to a structure.

8. The method of claim 5, wherein the bait station is installed by burying it partially or completely in-ground.

9. The method of claim 8, further comprising: III) adding more termiticidal bait matrix when the termiticidal bait matrix is exhausted or partially exhausted.

10. A method for controlling termites comprising:
I) monitoring for termite infestation by a process comprising
A) checking a bait station for signs of termites, wherein the bait station is installed in or near a locus of potential termite activity, and wherein the bait station contains a nontermiticidal bait matrix, and
B) determining that termites are present; and
II) installing in the bait station the termiticidal bait matrix of claim 1.

11. A termiticidal bait matrix comprising:
a) a termiticide comprising a cellulase inhibitor, wherein the cellulase inhibitor is selected from the group consisting of:
Bisphenol A diacetate, diammonium hexachloropalladate, 2-amino-3-[(phenylmethyl)thio]-1-propanol, bipenamol hydrochloride, compound having CAS Registry number 213193-76-1,

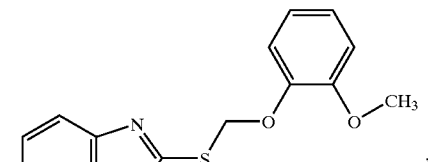

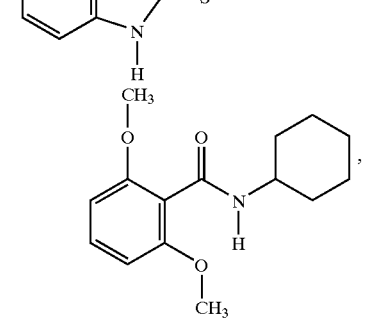

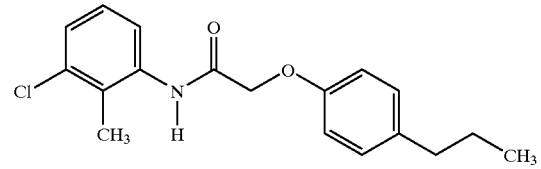

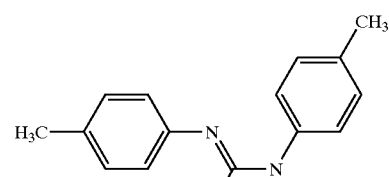

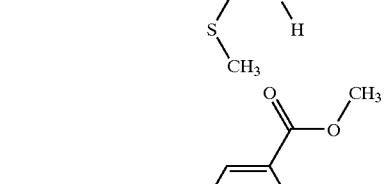

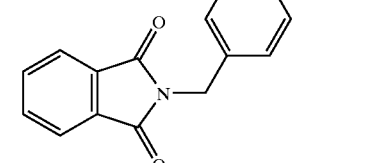

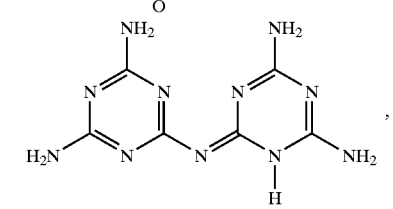

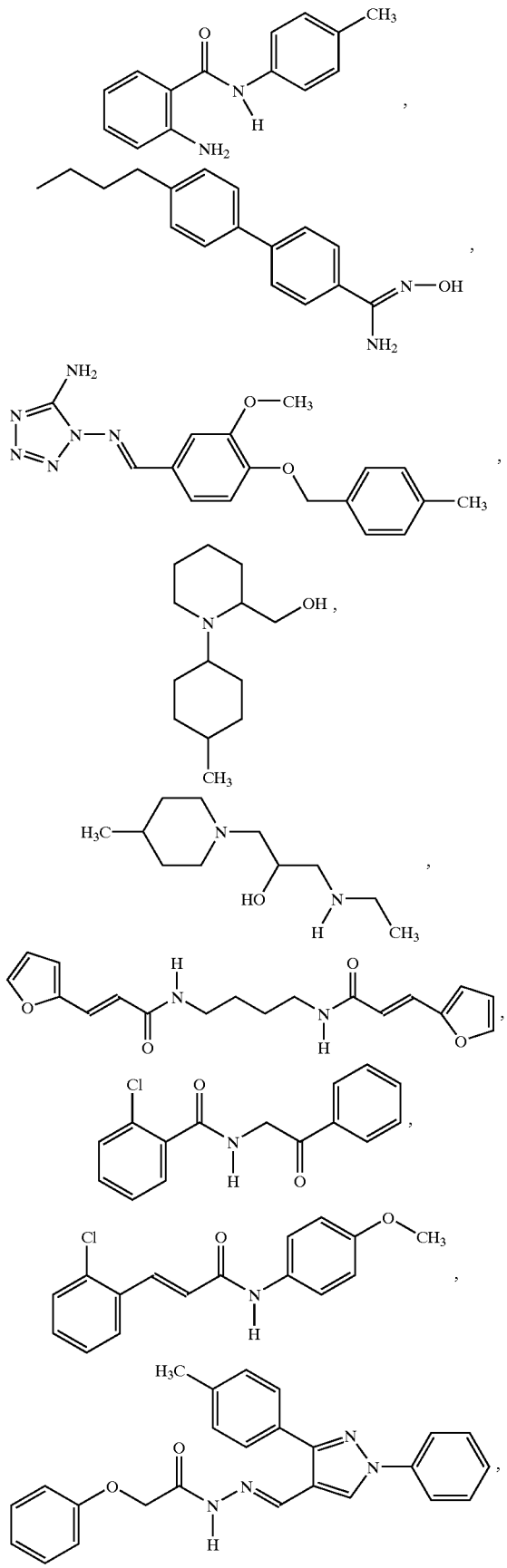
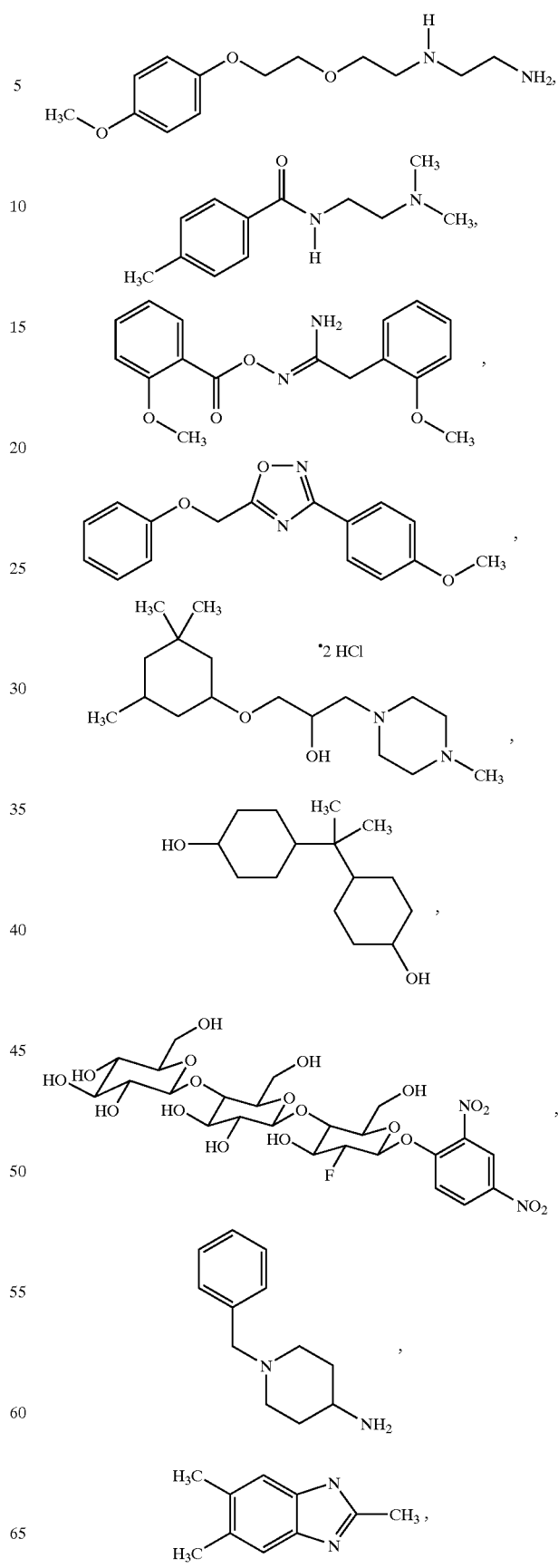

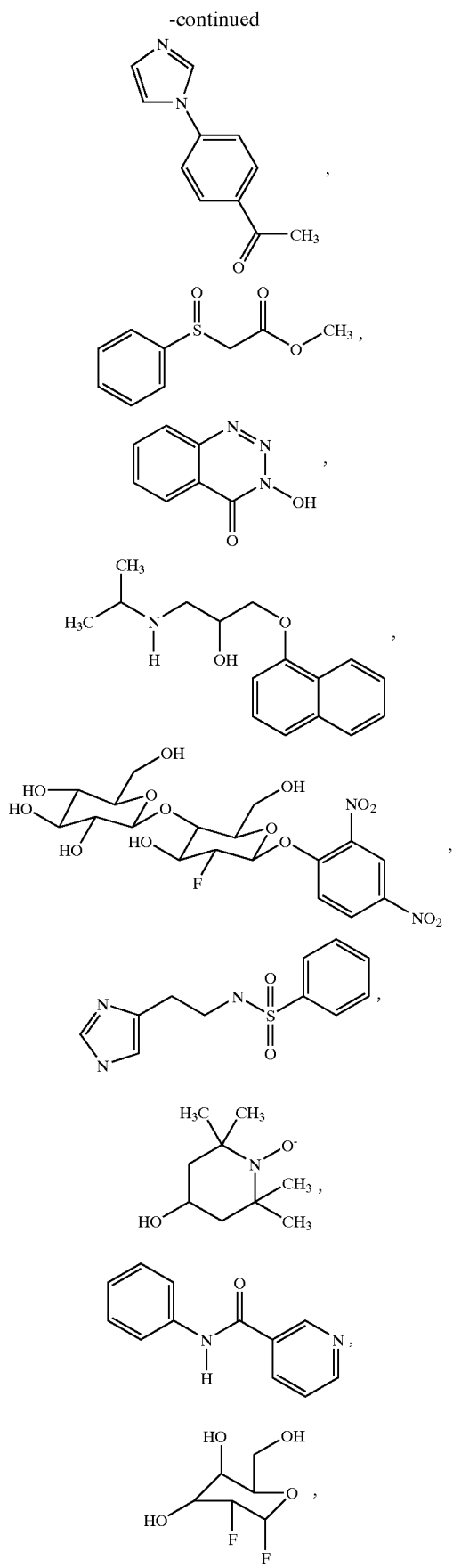

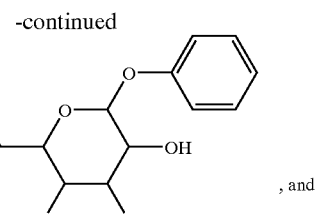, and combinations thereof, b) a cellulose containing material, and c) water wherein said termiticide is a cellulase inhibitor selected from the group consisting of: β-glucosidase inhibitors, endoglucanase inhibitors, exoglucanase inhibitors and combinations thereof.

12. The bait matrix of claim 11, wherein the cellulose containing material is selected from the group consisting of wood, charred wood, decayed wood, sawdust, pulp, paper, cotton linter, cellulose ethers, and combinations thereof.

13. The bait matrix of claim 11, further comprising:

d) one or more optional ingredients selected from the group consisting of attractants, defoamers, dextrin, dispersing agents, extenders, feeding stimulants, flavors, grain powder, moisture adjusting means, nitrogen sources, nutrients, penetrants, stabilizers, sugars, surface active agents, suspending agents, synergists, vegetable oils, and combinations thereof.

14. A termiticidal bait matrix comprising:

a) a termiticide selected so that the termiticide causes death to about 50 to about 100% of termites within about 24 to about 84 days after the termites begin to ingest the termiticide or the bait matrix comprising the termiticide, wherein the termiticide is an imidazole compound selected from the group consisting of:

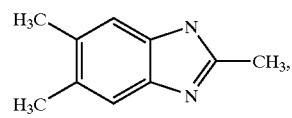

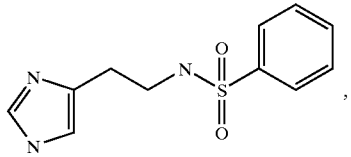

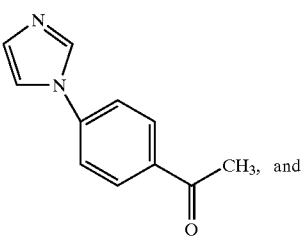, and

-continued

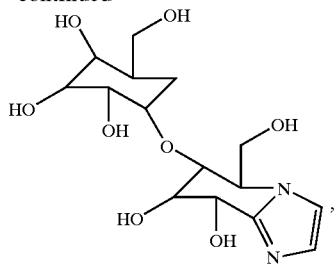

b) a cellulose containing material, and c) water wherein said termiticide is a cellulase inhibitor selected from the group consisting of: β-glucosidase inhibitors, endoglucanase inhibitors, exoglucanase inhibitors and combinations thereof.

15. A termiticidal bait matrix comprising:

a) a termiticide selected so that the termiticide causes death to about 50 to about 100% of termites within about 24 to about 84 days after the termites begin to ingest the termiticide or the bait matrix comprising the termiticide, wherein the termiticide is selected from the group consisting of -continued

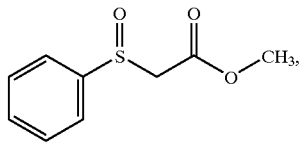

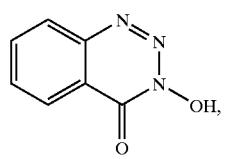

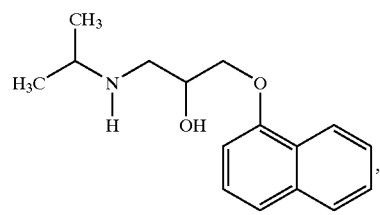

n-bromyl succinimide, 4,4'- isopropylidenedicyclohexanol, 2,5,6-trimethylbenzylimidazole, hexachloropalladate compounds, polyphenols, and combinations thereof, b) a cellulose containing material, and c) water wherein said termiticide is a cellulase inhibitor selected from the group consisting of: β-glucosidase inhibitors, endoglucanase inhibitors, exoglucanase inhibitors and combinations thereof.

* * * * *